US008200320B2

(12) United States Patent
Kovacs

(10) Patent No.: US 8,200,320 B2
(45) Date of Patent: Jun. 12, 2012

(54) INTEGRATED PHYSIOLOGIC MONITORING SYSTEMS AND METHODS

(75) Inventor: Gregory T.A. Kovacs, Palo Alto, CA (US)

(73) Assignee: PhysioWave, Inc., Palo Alto, CA (US)

( * ) Notice: Subject to any disclaimer, the term of this patent is extended or adjusted under 35 U.S.C. 154(b) by 1109 days.

(21) Appl. No.: 11/367,992

(22) Filed: Mar. 3, 2006

(65) Prior Publication Data
US 2007/0208233 A1    Sep. 6, 2007

(51) Int. Cl.
A61B 5/0402    (2006.01)
(52) U.S. Cl. ........................................ 600/513
(58) Field of Classification Search .......... 600/508, 600/509, 513
See application file for complete search history.

(56) References Cited

U.S. PATENT DOCUMENTS

| | | |
|---|---|---|
| 4,506,678 A | 3/1985 | Russell et al. |
| 4,920,489 A | 4/1990 | Hubelbank et al. |
| 5,126,967 A | 6/1992 | Simko |
| 5,206,602 A | 4/1993 | Baumgartner et al. |
| 5,231,990 A | 8/1993 | Gauglitz |
| 5,314,389 A | 5/1994 | Dotan |
| 5,330,513 A | 7/1994 | Nichols et al. |
| 5,382,956 A | 1/1995 | Baumgartner et al. |
| 5,448,997 A | 9/1995 | Kruse et al. |
| 5,467,090 A | 11/1995 | Baumgartner et al. |
| 5,504,684 A | 4/1996 | Lau et al. |
| 5,645,068 A | 7/1997 | Mezack et al. |
| 5,678,019 A | 10/1997 | Podkowa et al. |
| 5,678,562 A | 10/1997 | Sellers |
| 5,701,894 A | 12/1997 | Cherry et al. |
| 5,749,913 A | 5/1998 | Cole |
| 5,860,125 A | 1/1999 | Reents |
| 6,032,109 A | 2/2000 | Ritmiller, III |
| 6,047,203 A | 4/2000 | Sackner et al. |

(Continued)

FOREIGN PATENT DOCUMENTS
GB    2225459    5/1990

OTHER PUBLICATIONS

International Search Report and Written Opinion of the International Searching Authority for PCT International App. No. PCT/US07/63244.

(Continued)

Primary Examiner — Eric D. Bertram
(74) Attorney, Agent, or Firm — Law Office of Andrei D Popovici, PC

(57) ABSTRACT

In some embodiments, a wearable physiologic monitor comprises a mixed analog and digital application-specific integrated circuit (ASIC) including signal conditioning circuitry, an A/D converter, a real-time clock, and digital control logic. The signal conditioning circuitry includes analog amplification circuitry, analog (continuous-time or switched capacitor) filtering circuitry before the A/D converter, and in some embodiments digital (DSP) filtering circuitry after the A/D converter. The monitor includes sensors such as electrocardiogram (ECG) electrodes, accelerometers, and a temperature sensor, some of which may be integrated on the ASIC. The digital control logic receives digital physiologic data sampled at different rates, assembles the data into physiologic data packets, time-stamps at least some of the packets, and periodically stores the packets in a digital memory. The monitor may include a disposable patch including the ASIC, and a reusable, removable digital memory such as flash memory card. Applications include ambulatory monitoring and quantitative titration of care.

75 Claims, 8 Drawing Sheets

U.S. PATENT DOCUMENTS

| | | | |
|---|---|---|---|
| 6,080,110 | A | 6/2000 | Thorgersen |
| 6,117,077 | A | 9/2000 | Del Mar et al. |
| 6,128,520 | A | 10/2000 | Minoz |
| 6,135,951 | A | 10/2000 | Richardson et al. |
| 6,160,478 | A | 12/2000 | Jacobsen et al. |
| 6,168,563 | B1 | 1/2001 | Brown |
| 6,198,394 | B1 | 3/2001 | Jacobsen et al. |
| 6,243,574 | B1 | 6/2001 | McGregor et al. |
| 6,324,211 | B1 | 11/2001 | Ovard et al. |
| 6,385,473 | B1 | 5/2002 | Haines et al. |
| 6,416,471 | B1 | 7/2002 | Kumar et al. |
| 6,436,052 | B1 | 8/2002 | Nikolic et al. |
| 6,438,412 | B2 | 8/2002 | Ellenz |
| 6,440,069 | B1 | 8/2002 | Raymond et al. |
| 6,450,953 | B1 | 9/2002 | Place et al. |
| 6,454,708 | B1 | 9/2002 | Ferguson et al. |
| 6,495,230 | B1 | 12/2002 | do Canto |
| 6,539,253 | B2 | 3/2003 | Thompson et al. |
| 6,547,728 | B1 | 4/2003 | Cornuejols |
| 6,551,252 | B2 | 4/2003 | Sackner et al. |
| 6,582,365 | B1 | 6/2003 | Hines et al. |
| 6,594,759 | B1 | 7/2003 | Wang |
| 6,605,038 | B1 | 8/2003 | Teller et al. |
| 6,610,012 | B2 | 8/2003 | Mault |
| 6,640,134 | B2 | 10/2003 | Raymond et al. |
| 6,684,104 | B2 | 1/2004 | Gordon et al. |
| 6,685,634 | B1 | 2/2004 | Fry |
| 6,687,543 | B1 | 2/2004 | Isaac et al. |
| 6,755,783 | B2 | 6/2004 | Cosentino et al. |
| 6,790,178 | B1 | 9/2004 | Mault et al. |
| 6,810,350 | B2 | 10/2004 | Blakley |
| 6,811,538 | B2 | 11/2004 | Westbrook et al. |
| 6,847,892 | B2 | 1/2005 | Zhou et al. |
| 6,864,796 | B2 | 3/2005 | Lehrman et al. |
| 6,875,174 | B2 | 4/2005 | Braun et al. |
| 6,881,191 | B2 | 4/2005 | Oakley et al. |
| 6,895,278 | B1 | 5/2005 | Gordon |
| 6,895,280 | B2 | 5/2005 | Meadows et al. |
| 6,962,566 | B2 * | 11/2005 | Quistgaard et al. ............ 600/437 |
| 7,257,438 | B2 | 8/2007 | Kinast |
| 7,316,648 | B2 | 1/2008 | Kelly et al. |
| 7,382,247 | B2 | 6/2008 | Welch et al. |
| 7,384,410 | B2 | 6/2008 | Eggers et al. |
| 2001/0044588 | A1 | 11/2001 | Mault |
| 2003/0050537 | A1 | 3/2003 | Wessel |
| 2003/0088196 | A1 | 5/2003 | Steve |
| 2003/0126593 | A1 | 7/2003 | Mault |
| 2003/0130567 | A1 | 7/2003 | Mault et al. |
| 2003/0130595 | A1 | 7/2003 | Mault |
| 2003/0149349 | A1 | 8/2003 | Jensen |
| 2003/0197614 | A1 | 10/2003 | Smith et al. |
| 2004/0138517 | A1 | 7/2004 | Osorio et al. |
| 2005/0033124 | A1 | 2/2005 | Kelly et al. |
| 2005/0113703 | A1 * | 5/2005 | Farringdon et al. ............ 600/509 |
| 2005/0203349 | A1 | 9/2005 | Nanikashvili |
| 2005/0206518 | A1 | 9/2005 | Welch et al. |
| 2005/0283198 | A1 | 12/2005 | Haubrich et al. |
| 2006/0079942 | A1 | 4/2006 | Deno et al. |
| 2006/0122525 | A1 | 6/2006 | Shusterman |
| 2006/0154642 | A1 | 7/2006 | Scannell |
| 2006/0155589 | A1 | 7/2006 | Lane et al. |
| 2007/0055324 | A1 | 3/2007 | Thompson et al. |
| 2007/0069887 | A1 | 3/2007 | Welch et al. |
| 2007/0197878 | A1 | 8/2007 | Shklarski |
| 2008/0027679 | A1 | 1/2008 | Shklarski |
| 2008/0208009 | A1 | 8/2008 | Shklarski |

OTHER PUBLICATIONS

U.S. Appl. No. 11/367,155, Kovacs.

U.S. Appl. No. 11/368,290, Kovacs.

Discera, "Shrinking Wireless Architectures", available for download from www.discera.com prior to Mar. 3, 2006.

Mundt et al., "A Multiparameter Wearable Physiologic Monitoring System for Space and Terrestrial Applications", IEEE Transactions on Information Technology in Biomedicine, 9(3), Sep. 2005.

Atmel, "Microcontroller with 16 K Bytes In-System Programmable Flash", Atmel Amega, document contains notation AVR Jun. 2005.

Kaminska, "Wireless Wearable Biomonitors for Lifetime Wellness Optimization", Proceedings of the 3rd Annual International IEEE EMBS Special Topic Conference on Microtechnologies in Medicine and Biology, Kahuku, Oahu, Hawaii, May 2005.

NorthEast Monitoring Inc., "Holter LX Pro Software—Operator's Manual", NorthEast Monitoring Inc. Two Clock Tower Suite 360 Maynard Massachusetts 01754, Apr. 2003.

Nguyen et al., "Transceiver Front-End Architectures Using Vibrating Micromechanical Signal Processors", Dig. of Papers, Topical Meeting on Silicon Monolithic Integrated Circuits in RF Systems: 23-32, Sep. 2001.

ANSI/AAMI, EC11:1991/(R) 2001, Diagnostic Electrogardiographic Devices, 2000.

ANSI/AAMI, EC38:1998, Ambulatory Electrogardiographs, 1999.

Nguyen et al., "Frequency-Selective MEMS for Miniaturized Low-Power Communication Devices", IEEE Trans. Microwave Theory Tech 47(8):1486-1503, Aug. 1999.

Nguyen et al., "An Integrated CMOS Micromechanical Resonator High-Q Oscillator", IEEE Journal of Solid-State Circuits 34(4), Apr. 1999.

GeTeMed GmbH, "Baby Monitoring System VitaGuard VG3000", Teltow, Germany,1997-1999, available at http://www.fuse-network.com/fuse/demonstration/331/24571/24571.pdf.

Nguyen et al., "Micromachined Devices for Wireless Communications," Proc. IEEE 86(8):1756-1768, Aug. 1998.

Kovacs, "Micromachined Transducers-Sourcebook", McGraw-Hill, New York, New York, 1998.

Desel et al., "A CMOS Nine Channel ECG Measurement IC", ASIC 1996 2nd International Conference: 115-118, Oct. 1996.

Fraunhofer, "Medical Technology", available for download at http://web.archive.org/web/20051226133733/http://www.iis.fraunhofer.de/medtech/index.html, indicating webpage date of Dec. 26, 2005.

Toumaz AMx, "Technology", available for download at http://web.archive.org/web/20041207061227/www.toumaz.com/main.php?main=static&id=amx&header=technology, indicating webpage date of Nov. 8, 2005.

Kaminska, "Wearable Biomonitors With Wireless Network Communication", draft of paper published in Proceedings of the 3rd Annual International IEEE EMBS Special Topic Conference on Microtechnologies in Medicine and Biology, Kahuku, Oahu, Hawaii, May 2005.

Novosense Ab, "Company", available for download at http://web.archive.org/web/20050404122825/http://www.novosense.se/Company.htm, indicating webpage date of Apr. 4, 2005.

Imec, "Sensor Electronics", available for download at http://www.imec.be/wwwinter/mediacenter/en/SR2004/scientificreport/competences/c14/sr101_cont.html, Mar. 31, 2005.

Novosense Ab, "Technology", available for download at http://web.archive.org/web/20050209014154/http://www.novosense.se/technology.htm, indicating webpage date of Feb. 9, 2005.

Miromico Ag, "Sample Projects", available for download at http://www.miromico.ch/index.php?sec=ad.sa&lang=2, page includes notice of Copyright 2005 Miromico.

Mori, "Clinical Assessment of a New Method for Pacing Pulse Detection Using a Hybrid Circuit in Digital Holter Monitoring", Jpn Ciro J. 64(8): 583-9, Aug. 2000.

Pyron, "Pyron Introduces ECG ASIC Monitoring Subsystem", Electronic News: Nov. 29, 1999, available for download at http://www.edn.com/article/CA52794.html.

Nguyen et al, "An Integrated CMOS Mioromechanical Resonator High-Q Oscillator", IEEE Journal of Solid State Circuits 34(4), Apr. 1999.

Grossbach, "Measuring the ECG Signal With a Mixed Analog-Digital Application-Specific IC-Integrated Circuit, HP Component Monitoring System-Technical", Hewlett-Packard Journal, Oct. 1991, available for download at http://findarticles.com/p/articles/mi_m0HPJ/is_n4_v42/ai_11398513.

European Patent Office, Extended European Search Report Mailed Feb. 12, 2010 for EPO Application No. 07757854.0.

Office Action mailed May 28, 2009 for U.S. Appl. No. 11/367,155.

Office Action mailed Feb. 25, 2009 for U.S. Appl. No. 11/368,290.

CN China State Intellectual Property Office (SIPO), Office Action Mailed Oct. 13, 2010 for SIPO Patent Application No. 200780015788.1.

China State Intellectual Property Office, Office Action Mailed Oct. 13, 2010 for CN Patent Application No. 200780015788.1.

* cited by examiner

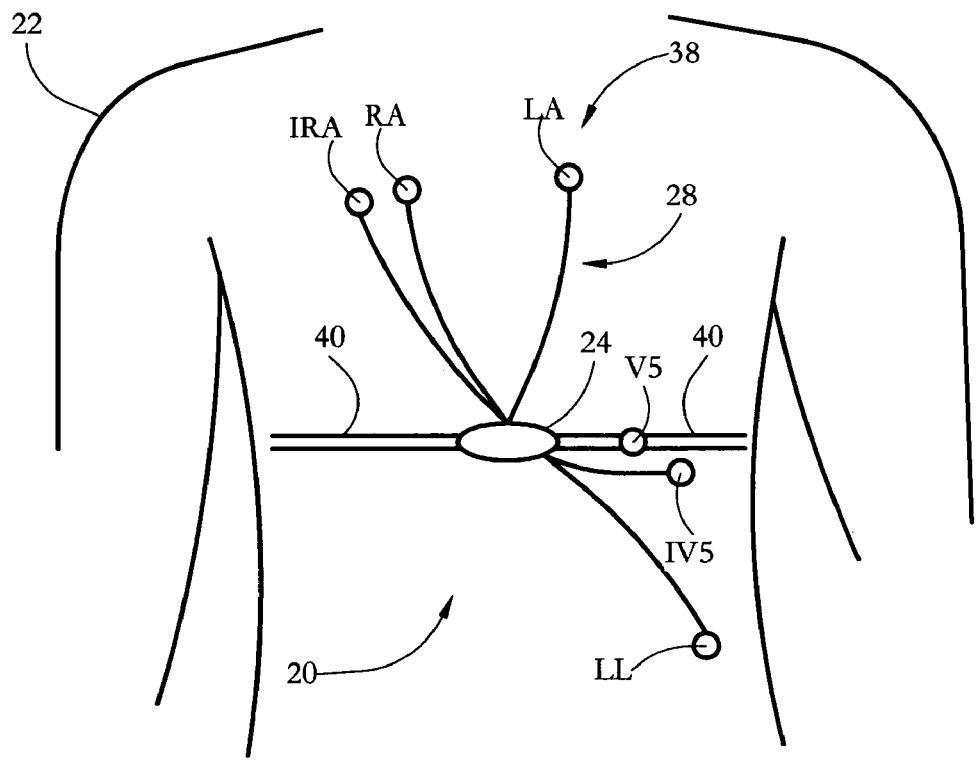
FIG. 1-A
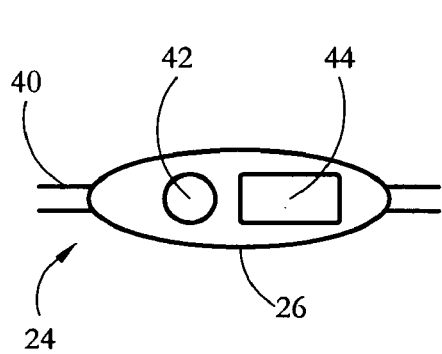
FIG. 1-B
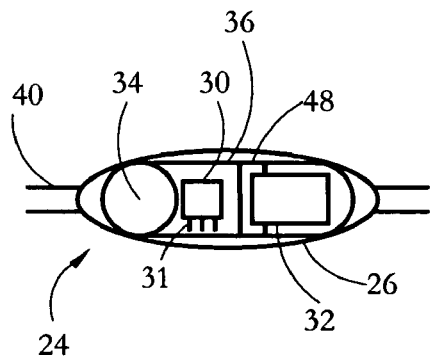
FIG. 1-C

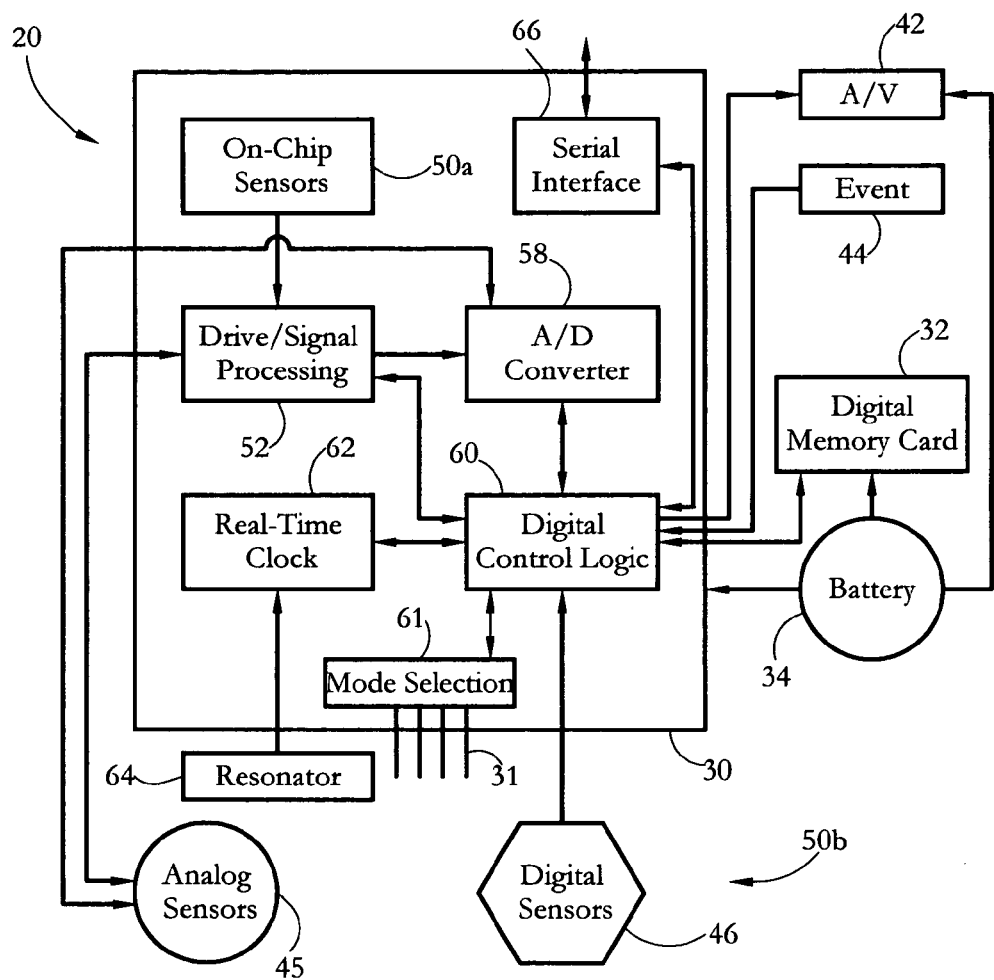
FIG. 2-A

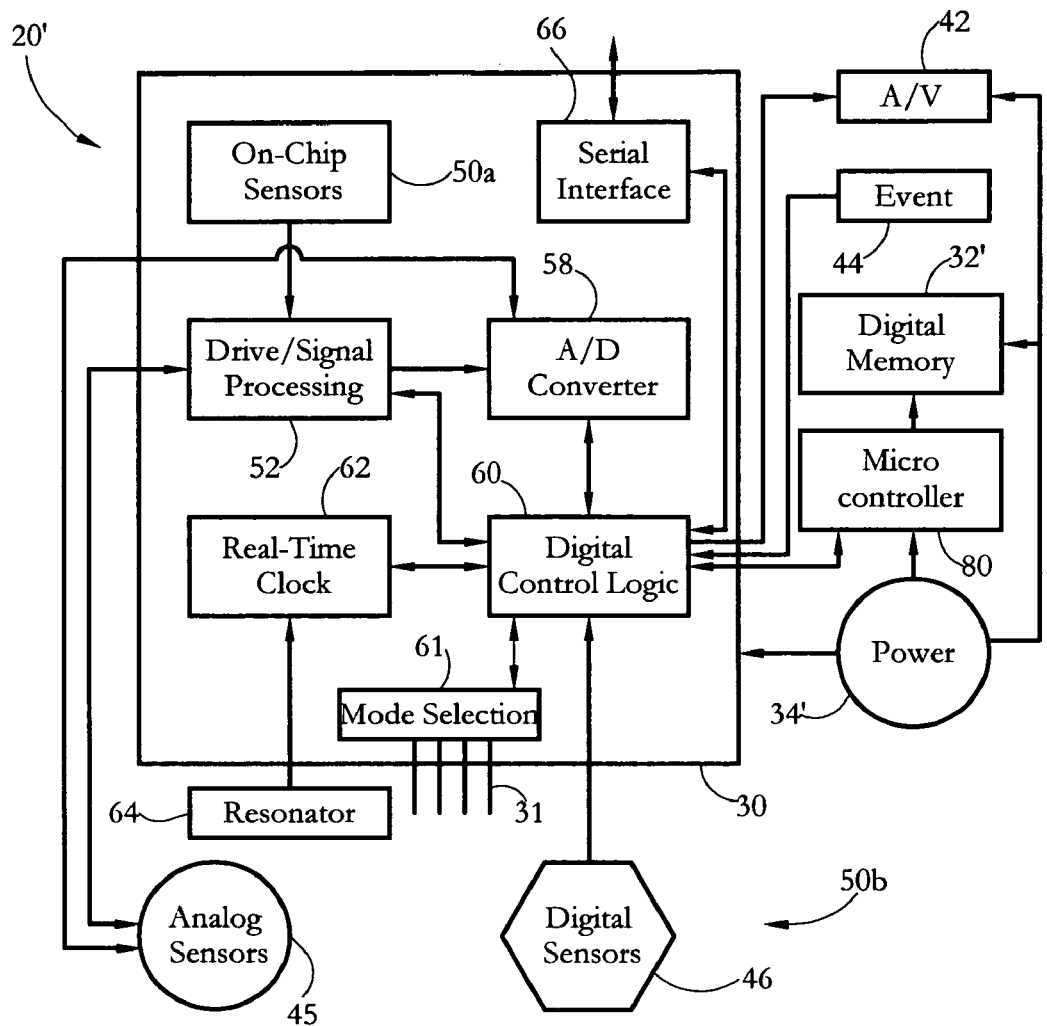
FIG. 2-B

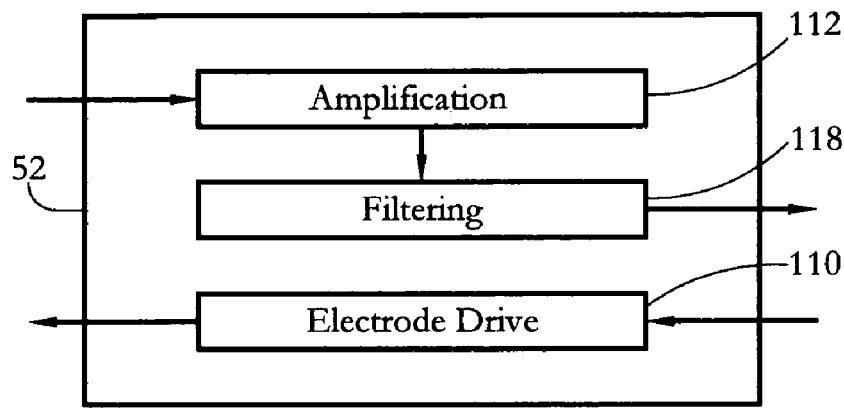
FIG. 3-A
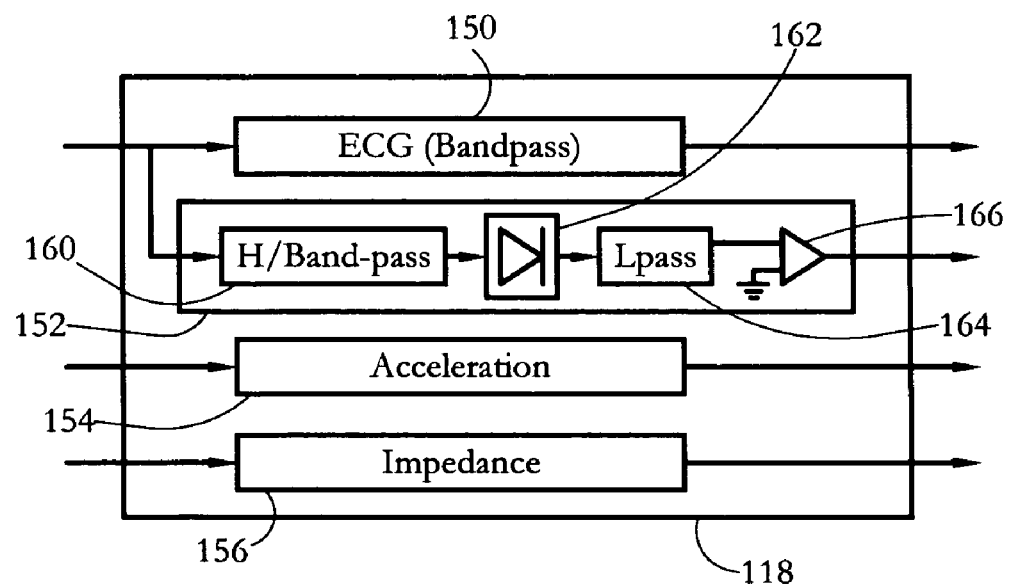
FIG. 3-B

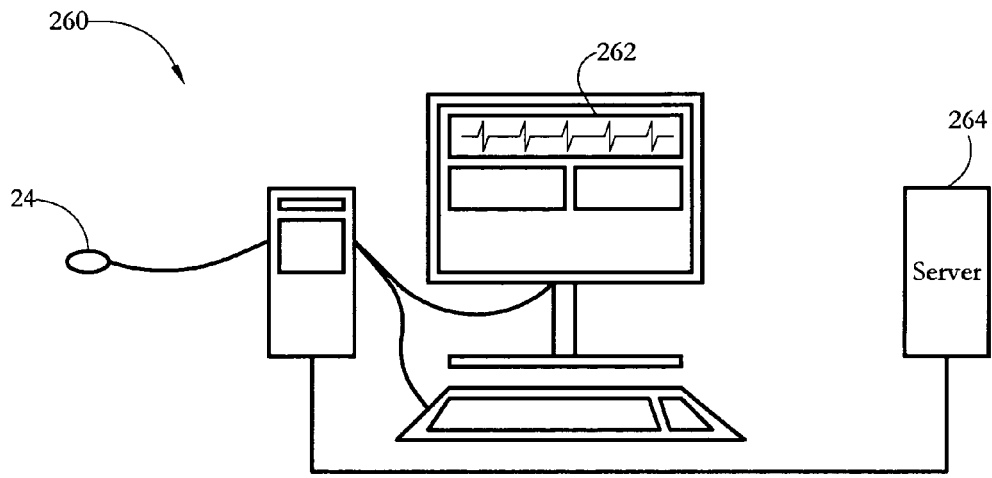
FIG. 6-A
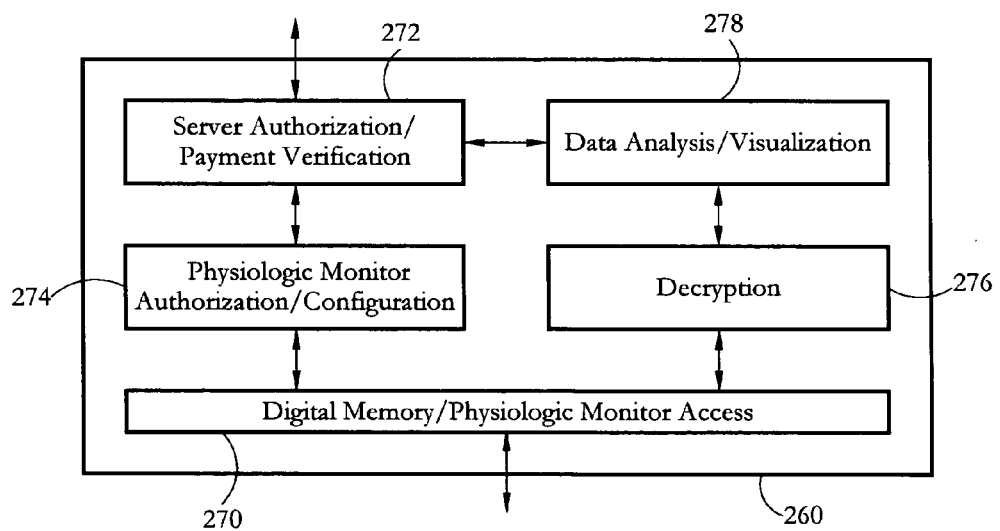
FIG. 6-B

INTEGRATED PHYSIOLOGIC MONITORING SYSTEMS AND METHODS

RELATED APPLICATION DATA

This application is related to U.S. patent application Ser. Nos. 11/367,155, entitled "Physiologic Monitoring Initialization Systems and Methods" and Ser. No. 11/368,280, entitled "Dual-Mode Physiologic Monitoring Systems and Methods," now U.S. Pat. No. 7,668,588, both by inventor Kovacs, G. T. A., which were filed concurrently with the present application.

BACKGROUND

The invention relates to physiologic monitoring systems and methods, and in particular to physiologic monitors.

Physiological monitoring instruments are used to measure a number of patient vital signs, including blood oxygen level, body temperature, respiration rate, and electrical activity for electrocardiogram (ECG) or electroencephalogram (EEG) measurements. In a common design used to perform ECG measurements, a number of electrocardiograph leads are connected to the patient's skin. Voltage variations are recorded over a period of time, and the resulting signals are processed, stored, and interpreted. The ECG signals of interest may be considerably lower in magnitude than environmental electrical noise levels generated by power lines, fluorescent lights, neighboring electrical devices, or electrolytic effects at the interface between the ECG leads and the patient's skin. The electrical signals sensed by the leads are commonly amplified and filtered in order to generate useful data.

A Holter monitor is an ambulatory electrocardiography device that allows heart monitoring for many hours or even days. Typical Holter monitors employ three to seven leads attached to a subject's skin. The monitor is commonly carried in a pocket or attached to a belt, and keeps a log of the heart's activity during a recording period.

A number of U.S. patents describe physiologic monitors, including portable ECG monitors. For example, in U.S. Pat. No. 5,701,894, Cherry et al. describe an ambulatory physiological computer recorder that includes multiple selective plug-and-play signal input conditioners, a microprocessor system with operating and analyzing software, and a removable memory module for data storage. System sensors may include electrodes for ECG, as well as sensors for measuring body temperature, respiration, skin conductance, and acceleration, among others.

In U.S. Pat. No. 6,198,394, Jacobsen et al. describe a system for remotely monitoring personnel status, including a plurality of sensors disposable on a soldier or other person for developing signals to determine the person's physiological status. Jacobsen et al. describe a wearable sensor unit including multiple sensors and a master controller or processor. Jacobsen et al. also describe employing a wrist sensor/display unit which may include multiple sensors and a controller connected to the sensors. The wrist unit is used in conjunction with a soldier unit carried by a soldier. The soldier unit also includes a controller, sensors, and other devices such as a global positioning system (GPS) device.

In U.S. Pat. No. 6,454,708, Ferguson et al. describe a system for monitoring health parameters and capturing data from a subject. The system includes a cordless sensor band with sensors for measuring full waveform ECG, full waveform respiration, skin temperature, and motion, and a connector which accepts a memory card or a smart card for storage of measured data.

SUMMARY

According to one aspect, a physiologic monitoring system includes a physiologic monitoring application-specific integrated circuit (ASIC) including an integrated real-time clock for generating a set of real time indicators; integrated amplification and filtering circuitry for amplifying and filtering a set of electrical signals received from a first set of physiologic sensors to generate a first set of filtered electrical signals; and integrated digital control logic connected to the real-time clock and the amplification and filtering circuitry. The amplification and filtering circuitry includes analog filtering circuitry for filtering the set of electrical signals received from the first set of physiologic sensors. The digital control logic is configured to receive a first set of digital physiologic data derived from the first set of filtered electrical signals, receive a second set of digital physiologic data, wherein the second set of physiologic data includes physiologic data sampled with a different sampling rate than the first set of digital physiologic data, generate a time-stamped physiologic data packet from a real-time indicator, the first set of digital physiologic data and the second set of digital physiologic data; and transmit the data packet for storage in a digital memory.

According to another aspect, a wearable physiologic monitoring system includes a battery, a plurality of electrocardiogram electrodes to be applied to a subject, a removable digital memory, and an ASIC including an integrated real-time clock for generating a set of real-time indicators, amplification and filtering circuitry connected to the plurality of electrocardiogram electrodes, for amplifying and filtering a set of electrical signals received from the electrocardiogram electrodes to generate a set of filtered electrocardiogram data, and digital control logic. The amplification and filtering circuitry includes analog filtering circuitry for filtering the set of electrical signals received from the electrocardiogram electrodes. The digital control logic is configured to assemble a time-stamped data packet including a set of digital electrocardiogram data derived from the filtered electrocardiogram data and transmit the data packet for storage in the removable digital memory. The data packet is time-stamped according to a real-time indicator.

According to another aspect, a wearable physiologic monitoring system comprises a digital memory, and a wearable patch including an integrated circuit connected to a plurality of electrocardiogram electrodes and the digital memory. The integrated circuit comprises a real-time clock for generating a set of real time indicators; a temperature sensor for generating a set of subject temperature indicators; an accelerometer for generating a set of subject acceleration indicators; amplification and filtering circuitry connected to the plurality of electrocardiogram electrodes, for amplifying and filtering a set of electrical signals received from the electrocardiogram electrodes; and digital control logic connected to the amplification and filtering circuitry, the temperature sensor and the accelerometer. The amplification and filtering circuitry includes analog filtering circuitry for filtering the set of electrical signals received from the electrocardiogram electrodes. The digital control logic is configured to assemble a physiologic data packet including digital electrocardiogram data derived from the set of electrical signals, temperature data derived from the set of subject temperature indicators, and acceleration data derived from the subject acceleration indicators, time-stamp the data packet according to a real-time indicator, and transmit the data packet to the digital memory for storage.

According to another aspect, a method of providing quantitative titration of care to a subject includes using a first wearable physiologic monitor to record a first set of physiologic data indicative of a first physiologic condition of a subject in a first treatment state. The first physiologic monitor includes a set of electrocardiogram sensors and a set of non-electrocardiogram physiologic sensors, a digital memory, and digital control logic connected to the electrocardiogram sensors, the non-electrocardiogram physiologic sensors and the digital memory. The digital control logic transmits physiologic data sensed by the electrocardiogram sensors and the non-electrocardiogram physiologic sensors for storage in the digital memory. The method further includes performing a first quantitative evaluation of the effect first physiologic condition according to the first set of physiologic data; recording a second set of physiologic data indicative of a second physiologic condition of the subject in a second treatment state; performing a second quantitative evaluation of the second physiologic condition according to the second set of physiologic data; performing a quantitative comparison of the first quantitative evaluation to the second quantitative evaluation; and making a treatment decision for the subject according to the comparison. The first and second treatment states may be states of the subject undergoing different courses of treatment, or states of the subject before and during/after a course of treatment.

BRIEF DESCRIPTION OF THE DRAWINGS

The foregoing aspects and advantages of the present invention will become better understood upon reading the following detailed description and upon reference to the drawings where:

FIG. 1-A shows a schematic view of a wearable physiologic monitor placed on a subject, according to some embodiments of the present invention.

FIG. 1-B shows a more detailed view of the physiologic monitor of FIG. 1-A according to some embodiments of the present invention.

FIG. 1-C shows a number of components of the physiologic monitor of FIG. 1-B according to some embodiments of the present invention.

FIG. 2-A is a diagram of the physiologic monitor of FIGS. 1-A-C in a stand-alone mode of operation, according to some embodiments of the present invention.

FIG. 2-B is a diagram of the physiologic monitor of FIGS. 1-A-C in a peripheral mode of operation, according to some embodiments of the present invention.

FIG. 3-A is a diagram of a signal drive and signal processing circuit of the physiologic monitor of FIGS. 1-A-C according to some embodiments of the present invention.

FIG. 3-B is a diagram of a filtering circuit of the circuit of FIG. 3-A according to some embodiments of the present invention.

FIG. 6-A shows an exemplary initialization and analysis console and an authorization server for a physiologic monitor according to some embodiments of the present invention.

FIG. 6-B shows a set of software subsystems of the initialization console of FIG. 6-A according to some embodiments of the present invention.

DETAILED DESCRIPTION OF PREFERRED EMBODIMENTS

Figure 4:
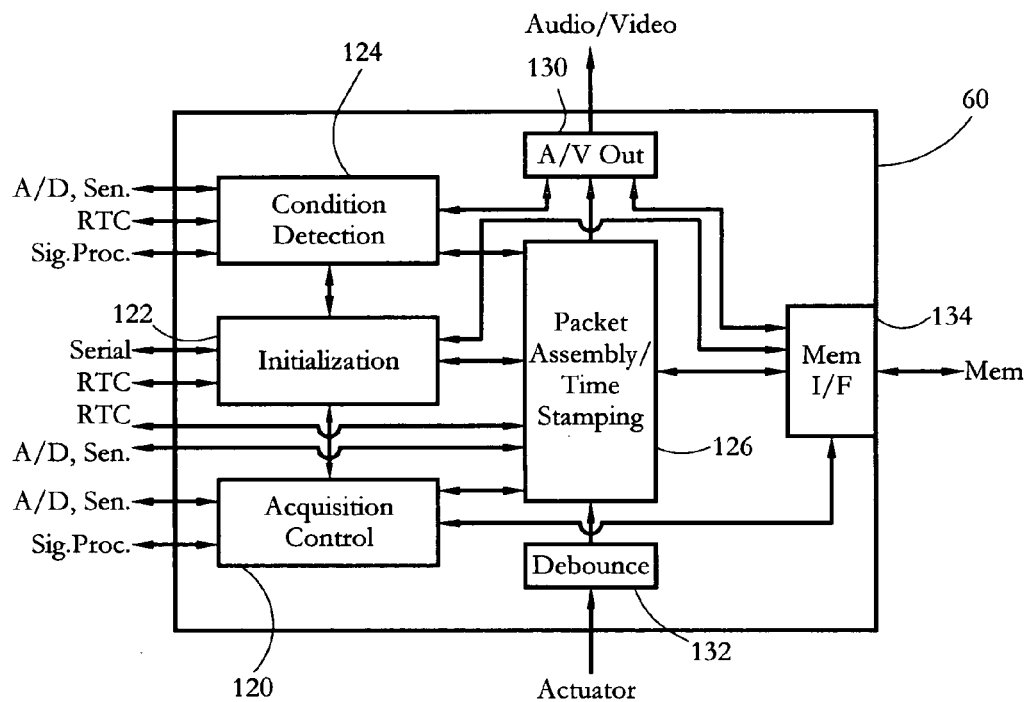
FIG. 4 is a diagram of an exemplary digital control logic unit of the physiologic monitor of FIGS. 1-A-C according to some embodiments of the present invention.

In the following description, it is understood that all recited connections between structures can be direct operative connections or indirect operative connections through intermediary structures. For example, digital control logic may be connected to amplification/filtering circuitry through an A/D converter. A set of elements includes one or more elements. A plurality of elements includes two or more elements. Any recitation of an element is understood to refer to at least one element. Unless otherwise specified, the term "logic" encompasses both dedicated (hardwired) logic and programmable logic such as logic implemented using field-programmable gate arrays (FPGA) or a programmable microcontroller. Unless otherwise specified, a wearable monitor encompasses monitors adhered to a subject (e.g. patches), as well as monitors loosely attached to a subject (e.g. through clothing, bands, string, a fanny pack, or other structures). Unless otherwise required, any described method steps need not be necessarily performed in a particular illustrated order. A first element (e.g. data) derived or generated from a second element encompasses a first element equal to the second element, as well as a first element generated by processing the second element and optionally other data. Generating a parameter of performing an action according to some data is not limited to generating the parameter or performing the action according only to that data, but encompasses using other data as well. An encapsulant is understood to be a generally-flexible material that encapsulates at least partially one or more enclosed components. Time-stamping first and second data encompasses applying a common time-stamp to a data packet including the first and second data, as well as separately time-stamping the first and second data with individual time-stamps. Time-stamping a data packet encompasses including an internal time-stamp within the packet, as well as associating an external time-stamp with the data packet. Unless otherwise specified, the statement that a digital memory is removable is understood to mean that the digital memory is removable by an end-user in the field by sliding or otherwise moving into and out of a mating position, without disassembling or destroying the memory or mating components. The statement that "amplification and filtering circuitry" includes a recited type of circuitry (e.g. continuous-time analog, switched capacitor, or DSP) means that at least some of the amplification and filtering circuitry includes the recited type of circuitry, and does not require both amplification circuitry and filtering circuitry to include the recited type of circuitry. Computer readable media encompass storage media such as magnetic, optic, and semiconductor media (e.g. hard drives, optical disks, flash memory, SRAM). The term "wide area network" encompasses the Internet as well as other networks including at least one router. Unless otherwise specified, the term "subject" encompasses both human and animal subjects. Unless otherwise specified, "home" use of a monitor refers to use during a normal course of activity of the subject and outside a medical setting (e.g. hospital or doctor's office), and is not limited to use at a home address of the subject. Replacing a first course of therapy with a second course of therapy encompasses employing a second course of therapy that is a modification of the first course of therapy (e.g. a modification in a medication dosage). Aspects of exemplary illustrated embodiments may contain patentable subject matter without regard to other aspects of the illustrated embodiments. Aspects of exemplary embodiments described below may be combined in ways other than the exemplary ways illustrated.

The following description illustrates embodiments of the invention by way of example and not necessarily by way of limitation.

FIG. 1-A shows a wearable physiologic monitoring system 20 placed on the skin of a subject 22, according to some embodiments of the present invention. Subject 22 may be a human or animal subject. Physiologic monitoring system 20 includes a wearable physiologic monitor 24, a plurality of subject electrical activity electrodes 38 attached to the subject's skin, and interconnections 28 connecting electrodes 38 to physiologic monitor 24. In some embodiments, electrical activity electrodes 38 include electrocardiogram (ECG) electrodes, as well as respiratory and/or fluid load impedance electrodes. The exemplary six-electrode configuration shown in FIG. 1-A includes LA (left arm), RA (right arm), IRA (respiratory/fluid load impedance RA), LL (left leg), V5 (left anterior axillary line in $5^{th}$ intercostal space), and IV5 (respiratory/fluid load impedance V5) electrodes. The LA, RA, LL and V5 leads are used for ECG measurements, while the IRA and IV5 leads are used for respiration and/or fluid load measurements. Other electrode configurations, including fewer or more electrodes and other electrode placements, are suitable for use in embodiments of the present invention. In some embodiments, electrodes 38 may include electroencephalogram (EEG) electrodes.

Interconnections 28 may include conductive wires with clips attached to electrodes 38. Physiologic monitoring system 20 may include additional physiologic and external parameter sensors, as described in detail below. Electrodes 38 are electrically connected to physiologic monitor 24. Physiologic monitor 24 may be formed by a patch held in place on the patient's skin by an underlying adhesive and/or a set of flexible straps 40. In some embodiments, physiologic monitor 24 is a disposable bandage unit, which may include encapsulated electrodes and electrode interconnections. In some embodiments, physiologic monitor 24 may include a case attached to external electrodes through wires.

FIG. 1-B shows a top view of physiologic monitor 24 according to some embodiments of the present invention. A sound and/or light indicator 42 and a user-activated event actuator (e.g. a button) 44 are situated on an outer surface of physiologic monitor 24. In some embodiments, indicator 42 includes an LED providing visual system status indicators to a user. Indicator 42 may also include a speaker emitting status and/or prompt sounds (e.g. beeps, music, synthesized speech) for the user. Indicator 42 may include a D/A converter, low-pass filter, and power amplifier connected in sequence between its input and the speaker and/or LED. In some embodiments, light/sound indicator 42 may be replaced by or used in conjunction with an additional annunciator capable of providing vibratory or other tactile stimulation. Event actuator 44 allows a user to mark events of note (e.g. falling, feeling faint, unusual feelings, taking medications) by pressing actuator 44. In some embodiments, user input actuators or controls may be provided in addition to actuator 44 to allow a user to enter a current date and time.

FIG. 1-C shows several components held within an encapsulant 26 of physiologic monitor 24. Encapsulant 26 may include a flexible material such as polyurethane. Encapsulant 26 partially encloses physiologic monitor 24, to provide mechanical protection to physiologic monitor 24 while allowing external access to indicator 42, event actuator 44, and a battery 34. Battery 34 may be sealed-in during a manufacture of physiologic monitor 24, or inserted into physiologic monitor 24 by a user. A flexible substrate 36 supports battery 34 and an application-specific integrated circuit (ASIC) 30. Integrated circuit 30 includes a set of input pins 31, some of which may be bonded to a given logic level (0, 1) configuration to set an operating mode of integrated circuit 30, as described below. Substrate 36 may include a non-conductive base and a set of conductive tracks (lines) formed on the base. In some embodiments, substrate 36 may be formed as described by Haines et al. in U.S. Pat. No. 6,385, 473, herein incorporated by reference.

A digital memory 32 is coupled to integrated circuit 30, and stores processed physiologic data in digital form, as described below. In some embodiments, digital memory 32 includes a flash memory card removably mounted in a memory card connector (socket) 48 defined along substrate 36. Suitable flash memory card formats include Compact Flash (CF) and xD-Picture card (xD), among others. In some embodiments, the digital memory may include a memory chip affixed to substrate 36. In some embodiments, the digital memory may include on-chip memory integrated with ASIC 30, as well as a non-removable, off-chip digital memory. In particular, in some embodiments, all data storage described below is performed in a removable memory card; in some embodiments, all data storage described below is performed in an on-chip memory; and in some embodiments, the bulk of measured physiologic data is stored in a removable memory card, while a set of configuration/initialization data is stored in an on-chip memory. Such configuration/initialization data may include settings and operational data such as firmware, subject ID, sensor sampling rates, authorization codes and data on authorized uses. An on-chip memory may also be used to provide temporary buffering of physiologic data while a memory card is exchanged.

Integrated circuit 30 is capable of operating in two or more alternative modes. Supported modes include a stand-alone mode, in which integrated circuit 30 stores data directly to digital memory 32, and a peripheral mode, in which integrated circuit 30 is used as a peripheral to a microcontroller. In some embodiments, the mode of operation is set during a mounting and connection of integrated circuit 30 on substrate 36, for example by bonding an input pin of integrated circuit 30 to one logic level (e.g. one, or $V_{dd}$) for one mode, and to another logic level (e.g. zero, or $V_{ss}$) for the other mode. Integrated circuit 30 may be set to the stand-along mode if it is to be used in a disposable, wearable product, and to the peripheral mode if it is to be used in a reusable (wearable or bedside) product.

FIG. 2-A shows a diagram of part of physiologic monitoring system 20 in a stand-alone mode of operation of integrated circuit 30, according to some embodiments of the present invention. Integrated circuit 30 includes a set of on-chip sensors 50a, a signal drive and signal processing circuit 52, an analog-to-digital (A/D) converter 58, digital control logic 60, mode-selection logic 61, a real-time clock 62, and an I/O port such as a serial interface 66. Real-time clock 62 is connected to a resonator 64. Resonator 64 may include an on-chip or off-chip timing resonator, and/or an off-chip quartz crystal.

A set of off-chip sensors 50*b* includes a set of sensors 45 having analog outputs, and a set of sensors 46 having digital outputs. Analog sensors 45 may include the electrical activity electrodes 38 shown in FIG. 1-A. In some embodiments, the set of on-chip sensors 50*a* includes an integrated temperature sensor and integrated three-axis accelerometers, while other sensors are provided off-chip. In some embodiments, the set of on-chip sensors 50*a* may include one or more of the sensor types described below. In some embodiments, the off-chip sensors 50*b* include one or more accelerometers and/or tilt sensors, an electrical or mechanical respiration and/or fluid load sensor, an off-chip temperature sensor, a pulse oximeter, a light intensity sensor, an ionizing radiation sensor, a galvanic skin resistance sensor, a joint-angle goniometer, a strain sensor, and/or an acoustic sensor. Such sensors are configured to detect parameters within physiologically-relevant ranges known in the art.

The temperature sensor is thermally coupled to the subject's skin, and provides real-time temperature data indicative of the subject's current temperature. In some embodiments, an on-chip temperature sensor may include an on-chip diode. Measuring a diode's forward voltage employs a diode's natural temperature sensitivity to provide a temperature indication. An on-chip temperature sensor may also employ a temperature-dependence of a bandgap voltage to provide a temperature indication. For information on junction-based temperature sensors, which may be integrated in a CMOS or bipolar integrated circuit, see for example "Thermal Transducers," Chapter 6 of Kovacs, G. T. A., "Micromachined Transducers Sourcebook," McGraw-Hill, Inc., New York, N.Y., 1998, pp. 570-577. Preferably, the reading provided by the on-chip temperature sensor is substantially-independent of the power dissipation of integrated circuit 30. Thus, preferably, the power dissipation of integrated circuit 30 is minimized, and the thermal coupling between the sensor and the subject is maximized, so as to minimize the effects of integrated circuit power dissipation on the temperature sensor output. In some embodiments, the temperature sensor is capable of measuring temperatures between 0 and 50° C. with an accuracy of 0.5° C. In some embodiments, a temperature sensor may include an ambient temperature sensor, a skin probe contacting the subject for skin temperature measurements, or a rectal probe for core temperature measurements.

The accelerometers provide real-time data on the relative position of the wearer (e.g. standing, supine), as well as his/her dynamic movements (e.g. walking, running, sleep, etc.). One or more accelerators may be provided for each of the x-, y- and z-axes. In some embodiments, the accelerometers are DC-responsive accelerometers capable of measuring acceleration values up to a predetermined threshold, which may be chosen to be between 2 g and 5 g. DC-responsive accelerometers are capable of measuring both constant and time-varying accelerations. Constant accelerations are steady-state accelerations, such as the gravitational acceleration. Measurement of such steady-state accelerations may be used to determine subject body orientations, i.e. standing vs. lying down. Time-varying accelerations may include accelerations caused by walking. The set of accelerators may include accelerators capable of determining acceleration values, as well as activity sensors, or switch-type accelerators, which detect whether an acceleration threshold has been exceeded. A switch-type accelerator may include a movable mass which closes a pair of switch contacts when the accelerometer is subjected to a sufficiently high steady-state or dynamic acceleration. Multiple switch-type accelerometers with different thresholds may be used along an axis, in order to provide information regarding the magnitude of sensed accelerations.

An impedance-based respiration and fluid load/hydration sensor is capable of detecting a trans-thoracic impedance of the subject by applying an alternating-current (AC) signal to one electrode placed on the subject's skin, and detecting the subject's response to the applied signal through another electrode placed on the subject's skin. The electrodes may include the IRA and IV5 leads shown in FIG. 1-A. The high-frequency part of the detected impedance is indicative of the subject's respiration, while the low-frequency or steady part of the impedance is indicative of the subject's fluid load/hydration. A mechanical respiration sensor may include a resistive band, applied to the subject's chest, having a resistance proportional to a subject chest's expansion. An exemplary respiration sensor may include a Procomp™ sensor, available from Thought Technology Ltd., West Chazy, N.Y.

A pulse oximeter is capable of detecting the subject's blood oxygen levels. A suitable pulse oximeter may include a Nonin® pulse oximeter (Nonin Medical Inc., Plymouth, Minn.), which may be attached to a finger, the forehead, or an ear lobe. Light intensity and acoustic sensors may be used to detect ambient light and sound levels, respectively. An ionizing radiation sensor may be used to detect levels of ionizing radiation such as gamma-radiation and X-ray energy. A galvanic skin resistance sensor may be used to measure the electrical resistance of the subject's skin, which depends on sweating, among other factors. A joint-angle goniometer may be used to measure the angle of a subject's joint. An exemplary joint-angle goniometer is available from ADInstruments, Inc., Colorado Springs, Colo.

A signal drive and signal processing (signal conditioning) circuit 52 is connected to on-chip sensors 50*a* and off-chip sensors 50*b*, including analog sensors 45 and digital sensors 46. FIG. 3-A shows a diagram of drive/processing circuit 52 according to some embodiments of the present invention. In response to enable signals received from digital control logic 60, a signal drive circuit 110 drives one or more analog sensors 45 (FIG. 2-A). For example, if analog sensors 45 include impedance-based respiration measurement electrodes, signal-drive circuit 110 provides an AC drive signal (voltage or current) to one of the electrodes. In some embodiments, signal drive circuit 110 is used, under the control of digital control logic 60, to identify inoperative ECG leads, such as leads that have may have become loose or been pulled off accidentally. Inoperative ECG leads are detected by an ECG fault detection circuit, which may include an AC signal (voltage or current) source, and a set of analog switches applying an AC test signal generated by the source to a selected ECG electrode being tested. An ECG lead fault is identified by measuring an impedance between the selected electrode and a reference (e.g. another electrode). An inappropriately high impedance value indicates that the ECG lead is disconnected or otherwise faulty.

An analog amplification circuit (amplifiers) 112 receives sensed signals from on-chip sensors 50*a* and off-chip analog sensors 45, and amplifies the received signals. A filtering circuit 118 filters the signals, which are then transmitted to A/D converter 58 (FIG. 2-A). In some embodiments, amplification circuit 112 and filtering circuit 118 may include multiple components used in parallel, for amplifying and filtering signals received from different types of sensors, which may correspond to different signal amplitudes, frequency content, and A/D sampling rates. Such components may include components used only in some configurations. For example, amplification circuit 112 and filtering circuit 118 may include circuitry capable of processing signals from twelve ECG leads and a number of sensor types described above, even though not all ECG leads and/or sensor types are used. A given sensor combination may be enabled by setting (e.g. bonding) a set of sensor configuration inputs (e.g. pins) of integrated circuit 30 to a combination of ones (e.g. $V_{dd}$, the circuit positive supply voltage) and zeros (e.g. $V_{ss}$, ground or the circuit negative supply voltage). An exemplary sensor set configuration may use only two of twelve available ECG leads. In a peripheral mode (described below with reference to FIG. 2-B), the sensor configuration mode of amplification circuit 112 and filtering circuit 118 may be set using a programmable internal register rather than bonded sensor configuration pins. In some embodiments, a given sensor combination may also be dynamically configured at a time of use, through digital control logic 60.

Amplification circuit 112 may include one or more voltage and/or transresistance (transimpedance) amplifiers, depending on whether voltage or current is sensed. Amplification circuit 112 may also include one or more differential amplification circuits, particularly for ECG signal processing. Amplification circuit 112 amplifies received signals so that the amplitude of the signal output to A/D converter 58 (FIG. 2-A) corresponds generally to the full-scale input signal of A/D converter 58. Generally, amplification circuit 112 is capable of amplifying received signals by a factor on the order of at least 10, e.g. by factors of hundreds or thousands. For example, if ECG signals received from electrodes 38 have a range on the order of ±5 mV, and A/D converter 58 has an input full scale on the order of 5 V, amplification circuit 112 may offset the input to 0-10 mV and amplify the resulting signal so that A/D converter 58 receives signals ranging from 0 to 5 V. Common CMOS A/D converters may have full-scale input voltages ranging from about $V_{ss}$ (e.g. ground) to $V_{dd}$ values such as 3.3 V or 5 V.

Filtering circuit 118 filters received signals, and transmits resulting signals to A/D converter 58. Filtering operations performed by filtering circuit 118 include anti-aliasing, noise-rejection, and band-shaping. Generally, the properties of filtering circuit 118 may be chosen according to the signal frequencies and sampling rates of interest, which may depend on a set of corresponding enabled sensors. At least parts of filtering circuit 118 are implemented using continuous-time analog circuitry including capacitors and resistors. In some embodiments, at least parts of filtering circuit 118 may be implemented using discrete-time analog circuitry such as switched-capacitor circuitry. In some embodiments, at least parts of filtering circuit 118 may be implemented using a digital signal processor (DSP); in such embodiments, an A/D converter may be used to digitize analog physiologic signals before input to the DSP filter, and front-end filtering circuitry may be provided to process signals before transmission to the A/D converter. In some embodiments, different parts of filtering circuit 118 may be implemented using continuous-time analog circuitry, switched capacitor circuitry, and/or a DSP. For example, filtering circuit 118 may include a continuous-time analog anti-aliasing and noise-rejection filter stage followed by subsequent continuous-time analog, switched-capacitor, and/or DSP band-shaping filters.

FIG. 3-B shows a diagram of filtering circuit 118 according to some embodiments of the present invention. In embodiments in which filtering circuit 118 includes a DSP, DSP parts of filtering circuit 118 may be downstream from A/D converter 58 (FIG. 2-A). Filtering circuit 118 includes an ECG signal filtering circuit 150, a pacemaker pulse detection circuit 152, an acceleration filtering circuit 154, and an impedance filtering circuit 156.

ECG signal filtering circuit 150 includes one or more bandpass filters that filter received data to reduce out-of-band noise and prevent aliasing. ECG signal filtering circuit 150 transmits the resulting signals to A/D converter 58 (FIG. 2-A). Common ECG filter cut-offs may be between 0.5 and 100 Hz. For a filter low-pass cut-off frequency of 100 Hz and a sampling rate of 256 samples/second (corresponding to a Nyquist frequency of 128 Hz), a filtering circuit with a roll-off of 72 dB between 100 Hz and 128 Hz may be used to attenuate undesired high-frequency signals below the dynamic range of a 12-bit A/D converter, with a 6 dB dynamic range per bit. In some embodiments, ECG filtering circuit 150 may include circuitry for carrying out inter-lead calculations such as deriving augmented ECG lead data by performing algebraic combinations using standard ECG lead data. For information on conventional frequency response specification data defined for ECG applications see for example the ANSI standard document "Ambulatory Electrocardiographs," ANSI/AAMI EC38-98. For descriptions of exemplary ECG filtering circuits see for example U.S. Pat. Nos. 5,206,602 and 5,382,956, which are herein incorporated by reference.

Pacemaker pulse detection circuit 152 detects pacemaker pulses, and outputs a sequence of digital pulses each corresponding to a pacemaker pulse. Pacemaker circuit 152 may be connected to one or more of the ECG electrodes 38 (FIG. 1-A). Pacemaker pulses are generally much narrower than normal ECG waveforms from the heart. In some embodiments, pacemaker pulse detection circuit 152 includes several circuits connected in series: a high-pass or band-pass filtering circuit (filter) 160, a rectification circuit (rectifier) 162, a low pass filtering circuit 164, and a comparator circuit 166.

Filtering circuit 160 may have a lower pass frequency on the order of kHz to tens of kHz (e.g. about 30 kHz), and a higher pass frequency on the order of tens to hundreds of kHz (e.g. about 100 kHz), to limit high-frequency noise. Rectification circuit 162 receives AC current and generates a rectified positive-voltage waveform. Low-pass filtering circuit 164 has a pass frequency on the order of Hz, for example about 5 Hz, chosen so as not to obscure or blur together individual pacing pulses. Low-pass filtering circuit 164 produces a pulsatile waveform, with each pulse corresponding to one pacemaker pulse signal. Comparator circuit 166 receives the pulsatile waveform, and outputs a digital output corresponding to each pacemaker pulse. Comparator circuit 166 may include a Schmitt trigger. In some embodiments, the output of low-pass filtering circuit 164 may be sent to A/D converter 58 (FIG. 2-A), where the pacemaker pulse detection signal is sampled at a rate on the order of tens of Hz (e.g. 50 Hz). For a description of an exemplary pacemaker pulse detection circuit see for example U.S. Pat. No. 5,448,997, which is herein incorporated by reference.

In some embodiments, acceleration filtering circuit 154 includes a low-pass filter. In some embodiments, impedance filtering circuit 156 includes a bandpass filter for reducing out-of-band-noise. The bandpass filter is followed by a homodyne or synchronous receiver, which mixes the signal received from the bandpass filter with a signal used by electrode drive circuit 110 (FIG. 3-A) to drive electrodes 38. The homodyne or synchronous receiver is followed by a low-pass filter. The output of the low-pass filter is a signal proportional to the detected impedance, which is rectified and transmitted to A/D converter 58.

In some embodiments, amplification circuit 112 and filtering circuit 118 include circuitry for detecting ECG lead faults.

A lead fault detection circuit may include an amplifier and a demodulator for measuring the impedance between a selected ECG lead and a reference, which may be another of the ECG electrodes, by measuring a level of a signal (voltage or current) detected in response to an application of an AC test signal using electrode drive circuit 110. The fault detection circuit may also include a threshold detection circuit which determines when a selected electrode impedance is above a predetermined threshold. For a description of an exemplary ECG fault detection circuit see for example U.S. Pat. No. 5,206,602.

A/D converter 58 (FIG. 2-A) receives filtered signals from drive/signal processing circuit 52, and generates corresponding digital signals for transmission to digital control logic 60. In some embodiments, A/D converter 58 may be a 12-bit, multi-channel, low-frequency, low-power device, for example a successive-approximation device or a sigma-delta device. A/D converter 58 is capable of digitizing signals received from multiple sensors, which may be sampled at different rates. A/D converter 58 is chosen so it is capable of digitizing at the maximum aggregate data rate from all sensors. For example, in some embodiments, ECG data is sampled at 256 samples/second, respiration data at 64 samples/second, and acceleration at 16 samples/second, while subject temperature, $SpO_2$, and heart rate are sampled at 1 sample/second. A/D converter 58 may include a multiplexer connected to multiple analog channels, for selecting a given data channel at a time for digitization. In some embodiments, A/D converter 58 may include a sample-and-hold circuit, which takes a snapshot of an analog signal and holds its value until its corresponding analog-to-digital conversion is completed.

Mode-selection logic 61 is connected to digital control logic 60 and input pins 31. Mode-selection logic 61 sets an operating mode of digital control logic 60 according to a logic level configuration of a set of mode-selection input pins 31. Available operating modes include a stand-alone mode, and passive and self-clocked peripheral modes, described in detail below.

Real-time clock 62 (FIG. 2-A) generates real-time digital time signals, which are transmitted to digital control logic 60. Real-time clock 62 may also generate date signals. An initial real time and date are set for real-time clock 62 during a system initialization, through digital control logic 60. In some embodiments, real-time clock 62 remains accurate within 0.01 seconds to 1 second, for example about 0.1 seconds, over 24 hours. In some embodiments, real-time clock 62 may receive periodic base timing signals from the main integrated circuit synchronization clock that provides synchronization clock signals to digital control logic 60 and other components of integrated circuit 30. In some embodiments, real-time clock 62 receives periodic base timing signals from timing resonator 64. In some embodiments, timing resonator 64 may be an external quartz crystal such as a 32,768 Hz crystal. In some embodiments, timing resonator 64 may be an on-chip silicon resonator integrated within circuit 30. For information on integrated MEMS silicon resonators see for example Nguyen et al., "An Integrated CMOS Micromechanical Resonator High-Q Oscillator," *IEEE J. Solid State Circuits* 34(4): 440-455, April 1999, Nguyen, "Transceiver Front End Architectures using Vibrating Micromechanical Signal Processors," *Dig. of Papers, Topical Meeting on Silicon Monolithic Integrated Circuits in RF Systems*, Sep. 12-14, 2001, p. 23-32, Nguyen et al., "Micromachined Devices for Wireless Communications," *Proc. IEEE* 86(8):1756-1768, August 1998, and Nguyen, "Frequency-Selective MEMS for Miniaturized Low-Power Communication Devices, *IEEE Trans. Microwave Theory Tech.* 47(8):1486-1503, August 1999.

Real-time clock 62 includes divider components (e.g. flip-flops, counters) for digitally dividing the received base timing signal to produce a real-time digital signal with a frequency of 1 Hz. For example, a 1-Hz real-time clock signal may be generated by dividing down a 2.097152 MHz integrated circuit synchronization clock signal by $2^{21}=2.097152\times10^6$, using twenty-one flip-flops connected in series. The 1 Hz tick signal is further input to one or more digital counters to generate a real-time digital time stamp transmitted to digital control logic 60.

A 1 Hz tick signal has a frequency which is of the same order of magnitude as some physiological frequencies of interest processed by signal processing circuit 52. Multiples of 1 Hz (e.g. 2, 4, 8 Hz, etc.) generated by a flip-flop divider chain may also be on the same order of magnitude as some physiological frequencies of interest. Preferably, signal processing circuit 52 is substantially unaffected by leakage or noise generated by real time clock 62. In some embodiments, the effects of real-time clock 62 on signal processing circuit 52 are reduced by physically distancing real-time clock 62 and signal processing circuit 52 along the surface of integrated circuit 30, for example by placing real-time clock 62 and signal processing circuit 52 along opposite sides of integrated circuit 30, or on opposite sides of other circuit units. Furthermore, in some embodiments a low-frequency real-time clock tick signal may include softened (e.g. obtuse, trapezoidal) edges, rather than square edges. A de-coupling off-chip capacitor, as well as separate power supplies, may be used in some embodiments to further isolate signal processing circuit 52 from real-time clock 62.

Serial interface 66 is connected to digital control logic 60 and real-time clock 62. Serial interface 66 allows connecting integrated circuit 30 bi-directionally to an external computer, to perform a number of initialization steps and/or to otherwise configure digital control logic 60. In some embodiments, serial interface 66 may also be used to connect digital control logic 60 to an external microcontroller (e.g. microcontroller 80, shown FIG. 2-B).

Sound/light indicator 42 and event actuator 44 are connected to digital control logic 60. Digital control logic 60 controls the visual and/or acoustic output of unit 42, and receives event signals from event actuator 44 for recording. Visual and/or acoustic indicators (e.g. LED blinking or changing color, speaker beeping, playing music or providing a spoken indication) are provided to indicate alerts or error signals, such as error signals indicating an improper positioning of electrodes, or warning signals indicating that monitored physiologic parameters are outside predetermined ranges. In some embodiments, sound/light indicator 42 comprises a speaker and a processing circuit connected to the speaker. The processing circuit may include a D/A converter, low-pass filter, and power amplifier connected in sequence between digital control logic 60 and the speaker.

Digital control logic 60 is further connected to digital memory 32. In some embodiments, digital memory 32 may be provided on-chip, integrated within circuit 30. In some embodiments, digital memory 32 comprises a non-volatile memory such as flash memory card, with a capacity sufficient to store the sensor data of interest over a period of about 24 hours or more. For example, a data rate of 100 samples per second at 2 bytes per sample corresponds to a daily storage requirement of about 17 MB. In such an application, a memory-having a capacity on the order of 32 to 64 MB would allow storing data over several days. Table 1 lists approximate storage requirements (in bytes) for several sampling rates and total storage periods, in a system using a 12-bit A/D converter and 2 bytes per sample.

TABLE 1

|  | Period | | |
| --- | --- | --- | --- |
|  | 24 hours | 48 hours | 7 days |
| Seconds/period | 86400 seconds | 172800 seconds | 604800 seconds |
| 100 samples/sec | $17.3 \times 10^6$ bytes | $34.6 \times 10^6$ bytes | $121.0 \times 10^6$ bytes |
| 200 samples/sec | $34.6 \times 10^6$ bytes | $69.1 \times 10^6$ bytes | $241.9 \times 10^6$ bytes |
| 500 samples/sec | $86.4 \times 10^6$ bytes | $172.8 \times 10^6$ bytes | $604.8 \times 10^6$ bytes |
| 1000 samples/sec | $172.8 \times 10^6$ bytes | $345.6 \times 10^6$ bytes | $1.2 \times 10^9$ bytes |

Battery 34 is connected to digital memory 32, sound/light indicator 42 and integrated circuit 30. In some embodiments, a DC voltage provided by battery 34 may be on the order of 0.5 V to 9 V. Battery 34 may be coupled to an on-chip charge pump (voltage converter) if an on-chip voltage higher than the voltage provided by battery 34 is needed. In some embodiments, multiple batteries may be connected to digital memory 32, sound/light indicator 42, and integrated circuit 30.

FIG. 2-B shows a diagram of part of a physiologic monitoring system 20' including integrated circuit 30 set in a peripheral mode of operation, according to some embodiments of the present invention. The peripheral mode of operation is particularly suited to bedside or other non-disposable device applications. In a peripheral mode of operation, digital control logic 60 is connected to a microcontroller 80. In some embodiments, microcontroller 80 is soldered down on a board, and connected to integrated circuit 30 through bonded pins. In some embodiments, microcontroller 80 may be connected to integrated circuit 30 through serial interface 66, through a special-purpose port of integrated circuit 30, or through the memory card connector otherwise used to connect a removable memory card to integrated circuit 30. Microcontroller 80 may be mounted in a socket defined along substrate 36 (FIG. 1-C). Microcontroller 80 is further connected to a power supply 34' and to a digital memory 32'. Digital memory 32' may include a memory card, a hard disk drive, random access memory (RAM), and/or other types of digital memory. Power supply 34' may include one or more batteries, as well as a power converter driven by power-line AC current.

In a peripheral mode, microcontroller 80 handles a number of functions otherwise performed by digital control logic 60, described in detail below. In some embodiments, a peripheral mode may include two sub-modes: a passive peripheral mode, in which digital control logic 60 is substantially inactive and microcontroller 80 manages most of the low-level functions of integrated circuit 30; and a self-clocked peripheral mode, in which digital control logic 60 performs a number of low-level functions described below, and generates hardware interrupts to microcontroller 80 in order to transfer assembled data packets to microcontroller 80 for further processing. The stand-alone (FIG. 2-A) and peripheral (FIG. 2-B) modes may be better understood by considering an exemplary configuration and operation of digital control logic 60.

FIG. 4 shows a diagram of digital control logic 60 according to some embodiments of the present invention. Digital control logic 60 is a finite state machine (FSM). The diagram of FIG. 4 shows an exemplary configuration of functional blocks implementing a functionality of digital control logic 60. The internal functional blocks of digital control logic 60 are shown in order to facilitate a systematic description of the functionality of digital control logic 60 according to some embodiments of the present invention, and not necessarily to imply required sharp structural boundaries within digital control logic 60. An engineer may generate a hardware description language (e.g. Verilog, VHDL) description of digital control logic 60 that can be synthesized and implemented into a structure generated by electronic design automation (EDA) software. Such EDA software may partition the functionality of digital control logic 60 in other ways than the exemplary configuration of FIG. 4.

The functional blocks of digital control logic 60 described below are connected and responsive to mode-selection logic 61 (FIG. 2-A). The description below will focus on the operation of digital control logic 60 in a stand-alone mode. In a peripheral mode, mode-selection logic 61 disables/bypasses at least some of the functional blocks of digital control logic 60 described below. For clarity, the data acquisition description below focuses on data received from A/D converter 58 (FIG. 2-A); additional data may be received from digital sensors 46 (FIG. 2-A).

Digital control logic 60 includes acquisition control logic 120, initialization logic 122, condition detection logic 124, packet assembly and time stamping logic 126 (for brevity, referred to below as packet assembly logic 126), audio/video output control logic 130, debounce and switch interface circuitry 132, and a digital memory interface 134. In some embodiments, digital control logic 60 is formed by hardwired logic. In some embodiments, digital control logic 60 may include a microcontroller core integrated on a common substrate with the other components of integrated circuit 30, including the hardwired logic of drive/signal processing circuit 52 (FIG. 2-A).

Digital memory interface 134 connects digital control logic 60 to digital memory 32 (FIG. 2-A). In particular, digital memory interface 134 receives time-stamped physiologic data packets from packet assembly logic 126, and directs the storage of the data packets in digital memory 32. Digital memory interface 134 may add formatting/file system information to each packet before storage. The formatting information may depend on the file system used to store data in digital memory 32. In some embodiments, a personal computer, DOS-compatible format such as a FAT16 or FAT32 format is used. Digital memory interface 134 selects a digital memory address for each packet to be stored. In some embodiments, selecting the address includes preventing overwriting data previously written to a removable memory by the present or another monitoring unit, such that the removable memory may be removed and re-inserted in and out of one or more monitoring units without causing substantial loss of data. Digital memory interface 134 determines the address of last-written data, and begins appending subsequent data following the last-written data, while maintaining a validly-formatted file. In some embodiments, digital memory interface 134 may support a single removable digital memory format. In some embodiments, digital memory interface 134 may support multiple removable digital memory formats, and may include pin-settable format selection logic for selecting a memory format to be used.

Initialization logic 122 is connected to serial interface 66 (FIG. 2-A), real-time clock 62, drive/signal processing circuit 52, A/D converter 58, and to a number of functional blocks of digital control logic 60 described below. In particular, initialization logic 122 is capable of connecting through serial interface 66 to an initialization console before physiologic monitoring system 20 becomes capable of acquiring and/or storing subject data.

FIG. 6-A shows an exemplary initialization and analysis console 260, which may be implemented using software running on a general-purpose computer. In some embodiments, console 260 is connected to physiologic monitor 24 during an initialization of physiologic monitor 24. In some embodiments, console 260 loads authorization data into digital memory 32 while the rest of physiologic monitor 24 is not connected to console 260, and physiologic monitor 24 is subsequently initialized by retrieving the authorization data from digital memory 32. In some embodiments, console 260 is also used to generate a physiologic data display 262 after a recording session has ended and data from digital memory 32 has been downloaded to console 260. In some embodiments, console 260 is provided in a physician's office or other medical facility. Console 260 is also able to connect to an external authorization server 264.

FIG. 6-B shows an exemplary structure of initialization console 260 according to some embodiments of the present invention. A digital memory/physiologic monitor access unit 270 controls communications with physiologic monitor 24 and/or digital memory 32 to perform an initialization of physiologic monitor 24 and subsequent downloads of physiologic data. In some embodiments, the initialization and physiologic data download steps described below are performed while only digital memory 32, without the rest of physiologic monitor 24, is connected to initialization console 260. Access unit 270 may then include software and/or a removable digital memory reader allowing access to digital memory 32. In some embodiments, the described initialization and/or download steps may be performed while integrated circuit 30 and/or microcontroller 80 (FIGS. 2-A-B) are connected to initialization console 260. Access unit 270 may then include software and/or a connector for connecting to physiologic monitor 24.

A server authorization and/or payment verification unit 272 connects initialization console 260 to external authorization server 264 (FIG. 6-A) over a communications link such as a secure wide area network (e.g. Internet) or telephone connection. Payment verification unit 272 submits to authorization server 264 payment data (e.g. a credit or debit card number, or another payment indication), physiologic monitor identity data (e.g. one or more serial numbers uniquely identifying corresponding non-enabled physiologic monitors) and user identity data (e.g. a user's name) for a set of physiologic monitoring uses. In some embodiments, the payor may be the subject, while in others the payor may be a person or entity different from the subject. The set of paid uses may include the entire set of monitoring uses supported by physiologic monitor 24, or a subset of the supported monitoring uses. Upon verifying that the user is authorized, for example if a payor has submitted a credit/debit card payment for a set of uses of physiologic monitoring system 20, authorization server 264 transmits to initialization console 260 a set of authorization and/or other initialization data for physiologic monitor 24.

In some embodiments, the authorization data includes a device-specific authorization code, as well as other subject- and session-specific authorization data. In some embodiments, a unique device-specific authorization code is required by physiologic monitor 24 in order to render physiologic monitor 24 user-operable to collect physiologic monitoring data, as described below. The authorization code identifies the stored data as originating from an authorized physiologic monitor. The authorization data may be traceable back to an individual physiologic monitor, subject, and payment authorization, in order to facilitate the creation of an audit trail. Initialization console 260 or an external server (e.g. authorization server 264) may pool large amounts of subject data belonging to different subjects and sessions and identified by unique authorization data. In some embodiments, a correspondence between authorization data and the subject's identity (e.g. name) is maintained remotely on a secure central server, for example in a health care provider's office, in order to protect the subject's privacy and maintain confidentiality even if the data stored in digital memory 32 were accessed by an unauthorized person.

In some embodiments, the authorization data identifies a subset of authorized uses (e.g. enabled sensor subsets), which may be uses that the subject has paid for, and/or uses relevant to a medical condition of the subject. For example, ECG measurements may be enabled for heart patients with arrhythmias, fluid load impedance measurements for patients suffering from congestive heart failure, respiratory impedance measurements for patients for whom respiratory monitoring is desired, and accelerometers for patients whose calorie expenditures are to be monitored or who are at risk of syncope. A number of sensor combinations or subsets may be employed according to desired applications.

A physiologic monitor authorization/configuration unit 274 transmits a set of authorization and/or configuration data to digital memory 32. The transmitted authorization and configuration data may include an authorization code, a physiologic monitor and/or subject ID, an encryption key identifier (an encryption key itself or other identifying data which may be used to retrieve or generate an encryption key), firmware, configuration settings for a number of components of physiologic monitor 24, an initial real date and time, audio/visual prompts, reminders and alerts, and other data. The transmitted authorization and configuration data is described in detail below with reference to initialization logic 122 (FIG. 4). In some embodiments, at least some of the transmitted authorization and/or configuration data may be received from authorization server 264, and at least some may be generated by authorization/configuration unit 274.

After physiologic monitor 24 has been used to record subject physiologic monitoring data for a period of time, digital memory 32 is re-connected to console 260 and the recorded data is downloaded to console 260. A decryption unit 276 (FIG. 6-B) receives from access unit 270 encrypted physiologic monitoring data recorded by physiologic monitor 24, and decrypts the data using a decryption key associated with the recording session. The decrypted data is transmitted to a data analysis/visualization unit 278, which generates physiologic data displays such as display 262 (FIG. 6-A). In some embodiments, data analysis/visualization unit 278 verifies that received physiologic data was recorded using an authorized physiologic monitor prior to data analysis/visualization. The verification process may include confirming that an authorization code, physiologic monitor ID and/or subject ID are authorized. The verification process may include connecting to authorization server 264.

On the physiologic monitor side, initialization logic 122 (FIG. 4) receives an initialization command and/or initialization data from console 260 or digital memory 32, and directs an initialization sequence in response to the initialization command and/or data, prior to performing physiologic measurements. In some embodiments, to prevent piracy, digital control logic 60 is not user-operable to collect physiologic monitoring data prior to the initialization sequence. In some embodiments, initialization steps include conducting a self-test and calibration sequence, conducting a device authorization sequence, downloading firmware to configure microcontroller 80, setting operating parameters to enable and/or configure signal processing circuit 52, digital control logic 60, and real-time clock 62, and writing initial configuration data to digital memory 32 if needed.

In some embodiments, initialization logic 122 performs a diagnostic self-test sequence including checking a voltage of battery 34, testing the ability of digital memory 32 to accept data (e.g. checking whether digital memory 32 is full and is working), checking sensor functioning by performing test measurements and/or fault detection steps for sensors 50*a-b*, checking analog and/or digital circuitry functioning, and storing testing results within integrated circuit 30 or in digital memory 32. Initialization logic 122 performs a calibration sequence including acquiring calibration data using sensors 50*a-b*, and storing calibration factors in memory, within integrated circuit 30 or in digital memory 32. The calibration factors include data generated from sensor measurements performed while physiologic monitoring system 20 is not connected to a subject.

In some embodiments, initialization logic 122 performs a device authorization sequence authorizing physiologic monitoring system 20 for a specific use. The device authorization sequence includes retrieving from initialization console 260 or digital memory 32 an authorization code and other authorization data to be associated with recorded physiologic data, and storing the authorization code and other authorization data in digital memory 32 and/or within digital control logic 60 if needed. As described above, in some embodiments initialization console 260 pre-loads digital memory 32 with authorization and/or configuration data, while digital memory 32 is removed from physiologic monitor 24; in such embodiments, initialization logic 122 retrieves the authorization data from digital memory 32. In some embodiments, the authorization data may be retrieved by initialization logic 122 directly from initialization console 260.

In some embodiments, initialization logic 122 renders physiologic monitor 24 operable to record physiologic data only if a predetermined, physiologic-monitor-specific authorization code is received. In particular, in some embodiments, a part of a programmable logic array forming part of initialization logic 122 is programmed at manufacture to include authorization code detection logic which responds only to a device-specific authorization code, and permits activation of physiologic monitor 24 if the correct authorization code is received.

In some embodiments, the authorization data may include or otherwise identify an encryption key to be used by packet assembly logic 126 to encrypt physiologic data before storage in digital memory 32. In some embodiments, the authorization data identifies a decryption key suitable for decrypting the physiologic data stored in digital memory 32. Such a decryption key identification may be provided to physiologic data analysis software, together with physiologic data stored in digital memory 32, for analysis after a recording session has ended.

In some embodiments, if a user has been determined to be authorized, initialization logic 122 retrieves from digital memory 32 or initialization console 260: firmware for microcontroller 80 (FIG. 2-B), configuration settings for digital control logic 60, and filter coefficients, topologies and/or state machine instructions for filtering circuit 118 if filtering circuit 118 includes DSP circuitry. In particular, microcontroller 80, digital control logic 60 and filtering circuit 118 may be operational only in a test mode or non-operational upon manufacture, and are only enabled to perform physiologic monitoring operations upon initialization. Digital control logic 60 may include a blank (re)programmable logic array that is only programmed during system initialization. For example, some logic functions of digital control logic 60 may be implemented using EEPROM or flash memory. In some embodiments, all of part of acquisition control logic 120, condition detection logic 124, and packet assembly/time stamping logic 126 (FIG. 4) may include parts of (re)programmable logic array. The firmware download and digital control logic and filtering circuitry programming provide additional piracy protection, since microcontroller 80 and integrated circuit 30 become capable of acquiring physiologic data only upon authorization by the initialization console. Allowing programming of parts of digital control logic 60 also facilitates future design changes.

Initialization logic 122 receives an initial time/date setting from initialization console 260, and uses the received initial time/date setting to set a current time/date for real-time clock 62 (FIG. 2-A). Setting configuration parameters for signal processing circuit 52 and digital control logic 60 may include setting sampling rates and enabling operating features. Enabling operating features may include defining an enabled sensor set and/or sensing operations (e.g. impedance sensing operations) to be performed by signal processing circuit 52 and digital control logic 60. An enabled sensor set may specify which sensor types or subsets (e.g. which ECG leads or other sensor types) are enabled for the authorized use. Different operating features and/or sampling rates may be enabled or set for different applications: for example, higher sampling rates may be used for monitoring the training of an elite athlete than for routine monitoring of an elderly patient or for veterinary uses. If filtering circuit 118 (FIG. 3-A) includes digital signal processing (DSP) circuitry, setting configuration parameters for signal processing circuit 52 may include programming filter coefficients, topologies, and/or state machine instructions to customize and render operable signal processing circuit 52 upon initialization.

Initial configuration data written to digital memory 32 may include an authorization code, described above, as well as a physiologic monitor and/or subject ID. In some embodiments, initial configuration data written to digital memory 32 includes configuration parameters (e.g. enabled operating features, sampling rates) for signal processing circuit 52 and digital control logic 60. Initial configuration data written to digital memory 32 may further include customized audio/visual alarms, prompts, and reminders to be played back to the user, as well as configuration settings for the stored audio/visual data. Audio prompts may include spoken reminders to take medicines, to remove monitoring unit 20 and/or digital memory 32 when digital memory 32 is full or when a programmed recording session is over, and indications of sensor faults or physiologic parameter conditions (e.g. a warning of a high measured heart rate, or praise for meeting a target exercise heart rate). In some embodiments, audio prompts are recorded using a voice such as the voice of the subject, a family member, a medical professional (e.g. the subject's family doctor or a familiar nurse), a public personality (e.g. an actor or professional athlete), a simulated famous person, or a cartoon character. In some embodiments, programmed speech data includes data personalized with both the user's identity, and with a number of speech messages tailored to a sensor subset or application. For example, if the user's name is Bob, and if Bob's physiologic monitor uses a set of ECG leads, programmed speech data may include a phrase such as "Bob, a lead has fallen off!" Audio prompts may also include music and/or sound effects. In some embodiments, configuration settings for the stored audio/visual data include audio volume configuration data causing the volume of audio output to be softer at predetermined times (e.g. during traditional sleep hours), or louder for patients who are hard of hearing.

Acquisition control logic 120 includes logic controlling the operation of A/D converter 58 and signal processing circuit 52 (FIG. 2-A) according to a number of configuration parameters, including parameters defining the analog signals to be processed and their sampling rates. In embodiments in which signal processing circuit 52 uses analog circuitry, acquisition control logic 120 mainly handles the timing of A/D converter 58. In particular, acquisition control logic 120 sends selection signals to a multiplexer of A/D converter 58, to determine which of multiple analog signals is to be digitized. If A/D converter 58 includes a sample-and-hold circuit, acquisition control logic 120 sends hold pulses or sets hold logic levels to direct the sample-and-hold circuit to hold given analog signals. Acquisition control logic 120 further sends digitization commands to A/D converter 58, directing A/D converter 58 to digitize data from a given signal channel. For example, if A/D converter 58 is a successive approximation device, acquisition control logic 120 may send a start digitization signal to A/D converter 58 to begin digitization of a sample. In some embodiments, a sample is considered ready following a predetermined number of synchronization clock cycles after its digitization start. In some embodiments, a sample is considered ready when a sample ready signal is received from A/D converter 58.

In embodiments in which signal processing circuit 52 uses switched capacitor signal processing, acquisition control logic 120 may additionally provide a clock signal or signals to filter elements of signal processing circuit 52. Hardwired logic within signal processing circuit 52 of acquisition control logic 120 may be used to provide desired switching frequencies to the filtering elements of signal processing circuit 52.

In embodiments in which signal processing circuit 52 uses digital signal processing, acquisition control logic 120 may additionally be used to route a continuous sample stream to different filter channels, load and/or recirculate filter coefficients and resulting intermediate data, and carry out inter-lead calculations such as deriving augmented ECG lead signals by performing algebraic combinations of standard ECG lead signals.

Condition detection logic 124 receives signals from A/D converter 58, signal processing circuit 52, and real-time clock 62, and detects whether predetermined physiologic conditions, real-time conditions, and/or sensor faults or other conditions have occurred. Condition detection logic 124 may also be used to control electrode drive circuit 110 (FIG. 3-A) to apply AC fault detection signals to selected ECG electrodes. ECG lead fault detection steps may be performed after an initial placement of the ECG electrodes on the subject, and at periodic intervals thereafter. In some embodiments, condition detection logic 124 determines whether a measured impedance between a selected ECG lead and a reference (e.g. another ECG lead) exceeds a predetermined threshold. In some embodiments, condition detection logic 124 determines whether physiologic data received from A/D converter 58 (e.g. a measured subject temperature or heart rate, measured ionizing radiation levels, estimated calorie expenditures derived from accelerometer data) are outside predetermined ranges or otherwise meet predetermined conditions. In some embodiments, condition detection logic 124 determines whether a current real time and a measured ambient light level meet predetermined conditions (e.g. have predetermined values, or are lower or higher than predetermined values). Condition detection logic 124 sends condition indicators, which may include indicators of fault or other condition types, to audio/video output control logic 130 and to packet-assembly logic 126. For example, when an estimated calorie expenditure during an exercise period has exceeded 300 calories, condition detection logic 124 may send a corresponding condition indicator to output control logic 130 in order to provide encouragement to the subject. When a real time is sufficiently late and/or a detected ambient light level is sufficiently low, condition detection logic 124 may send a quiet-volume indicator to output control logic 130, in order to lower the volume or mute audio indicators. For ECG data, a sensor fault may include an indicator that one or more ECG leads have fallen off or are not connected properly. The fault indicators may be used by audio/video output control logic 130 to generate audio and/or visual warnings to a user. The condition indicators may be used by packet assembly logic 126 to include condition-detection flags in corresponding data packets, as described below.

Packet-assembly logic 126 receives data streams corresponding to different physiologic data types from A/D converter 58 and digital sensors 46, and real-time indicators from real-time clock 62 (FIG. 2-A). The data streams are received at different rates. Packet-assembly logic 126 assembles the received data into formatted packets for transmission to memory interface 134, to be stored into digital memory 32 (FIG. 2-A). Packet-assembly logic 126 includes one or more buffers for storing assembled data before transmission to memory interface 134. Each packet sent to memory interface 134 includes a set of physiologic data of interest, a set of data types, associated time stamps, and a fault detection flag.

In some embodiments, packets are stored in digital memory 32 at regular intervals, for example one packet every second. A packet may include physiologic data of different types, sampled at different rates. For example, an exemplary packet stored every second may include 512 ECG samples (256 samples per second for 2 leads), 64 respiratory impedance samples, 48 acceleration samples (16 each of 3 axes), and other samples such as one or two $SpO_2$ samples, an event marker, and light, acoustic, ionizing radiation, and joint-angle goniometer samples. The ECG samples may be 12-bit samples, while other samples may be 8-bit samples. Together with time stamp and formatting data, such an exemplary packet may include on the order of a thousand bytes.

Figure 5:
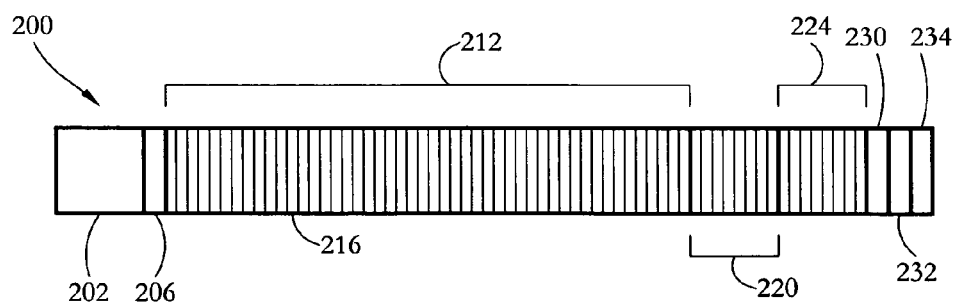
FIG. 5 shows exemplary data packet contents according to some embodiments of the present invention.

FIG. 5 shows the contents of an exemplary physiologic data packet 200 according to some embodiments of the present invention. Packet 200 includes a formatting field 202, a time-stamp field 206, an ECG data field 212 including multiple ECG data samples 216, other physiologic data fields 220, 224, 230, 232, and an event marking and fault detection field 234.

In some embodiments, each stored packet is time-stamped by including a real-time indicator in the packet. In some embodiments, at least some of the packets need not include stored time-stamps; rather, the time of each packet can be extracted from its ordered position relative to a time-stamped packet. For example, if an initial packet is time-stamped with an initial real time, and one packet is stored every second, a 10$^{th}$ packet following the initial packet can be associated with a real-time of 10 seconds following the initial real time. In some embodiments, a time stamp is inserted into any packet that includes an indicator of an external event signaled using event actuator 44 (FIG. 2-A). In some embodiments, asynchronous events such as external event markers are marked by inserted flags, rather than explicit time-stamps. In some embodiments, time-stamps are inserted periodically in the packet sequence. In some embodiments, a time-stamp is inserted in a final packet any time recording is paused or ended, and in a first packet any time recording is started or resumed.

In some embodiments, packet assembly logic 126 or memory interface 134 may include encryption logic for encrypting physiologic monitoring data prior to storage in digital memory 32. The encryption logic may implement a cipher such as a symmetric key cipher (e.g. RC4, AES), or a public-key cipher (e.g. RSA).

Audio/video output control logic 130 generates driving signals for light/sound indicator 42 (FIG. 2-A), in response to trigger signals received from condition detection logic 124 and digital memory 32, and in response to real-time data received from real-time clock 62. In some embodiments, A/V output control logic 130 comprises audio decoding logic capable of decoding audio (e.g. speech) data stored in digital memory 32. Speech data may be programmed in digital memory 32 during a system initialization, which may include steps such as setting the system real-time clock. In some embodiments, A/V output control logic 130 comprises logic configured to compare locally-stored time reference values to real-time data received from real-time clock 62, and to generate driving signals when pre-set comparison conditions are met (e.g. every N minutes or hours, or at predetermined times/dates). A/V output control logic 130 sends decoded digital signals to a digital-to-analog converter (DAC), which may be provided as part of integrated circuit 30 or light/sound indicator 42.

The driving signals generated by A/V output control logic 130 may include signals driving light/sound indicator 42 to flash an LED or change the LED display color, generate beeps, play music, or play digitized or synthesized voice prompts. Data used to generate the driving signals may include data hard-coded within integrated circuit 30 and/or data stored in digital memory 32. In some embodiments, A/V output control logic 130 checks for a value of a digital speech flag in digital memory 32. If the flag is set to an enabled value, A/V output control logic 130 retrieves the speech for transmission to light/sound indicator 42. The digital speech flag is set during the system initialization.

Debounce and switch interface circuitry 132 receives external, analog event signals from event actuator 44 (FIGS. 2-A-B), and generates a clean digital event marker signal. The event marker signal is transmitted to packet assembly logic 126 for assembly into an associated packet. In some embodiments, debounce and switch interface circuitry 132 may be external to digital control logic 60.

If integrated circuit 30 is configured in a stand-alone mode, the various parts of digital control logic 60 described above are active. If integrated circuit 30 is configured in a peripheral mode, at least some of the parts of digital control logic 60 are bypassed/disabled. In a self-clocked peripheral mode, packet assembly logic 126 generates a hardware interrupt to microcontroller 80 when an assembled data packet is ready. In the self-clocked peripheral mode, digital control logic 60 transfers data to microcontroller 80 for further processing and/or storage, rather than directly to digital memory 32. Microcontroller 80 receives the assembled data packets, performs further processing on the data, and stores resulting data in a digital memory. In a passive peripheral mode, microcontroller 80 (FIG. 2-B) performs the functions described above for digital control logic 60, and digital control logic 60 is essentially disabled/bypassed. For example, in the passive peripheral mode, microcontroller 80 may provide synchronization timing signals to real-time clock 62, supply digitized speech data to light/sound indicator 42, control the timing of A/D converter 58, control drive/signal processing circuit 52 to generate signals used for impedance measurements and fault detection.

In some embodiments, an initialization sequence as described above is performed according to the operating mode of integrated circuit 30. In particular, if integrated circuit 30 is configured in a stand-alone mode, in some embodiments the initialization sequence may not include downloading firmware for microcontroller 80. If integrated circuit 30 is configured in a passive peripheral mode, the initialization sequence may not include configuring digital control logic 60. If integrated circuit 30 is configured in a self-clocked peripheral mode, the initialization sequence may include both downloading firmware for microcontroller 80 and programming a programmable logic array within digital control logic 60.

In some embodiments, if integrated circuit 30 is configured in a peripheral mode, an initialization sequence as described above may be performed according to communications between microcontroller 80 and initialization console 260 (FIG. 6), while initialization logic 122 (FIG. 4) remains inactive. Microcontroller 80 may be connected to initialization console 260, placed in a circuit program mode, and the entire operating firmware for microcontroller 80 may be downloaded to internal memory or digital memory 32. Prior to initialization, microcontroller 80 may be blank, in order to make firmware piracy more difficult. After the initial programming, microcontroller 80 may allow changes to physiologic monitor configuration parameters such as enabled sensor set, sampling rates, real time, encryption key, authorization codes, subject/device IDs, voice/sound prompts, and other customization data stored in digital memory 32 or microcontroller 80, while disallowing changes to the firmware.

In some embodiments, initialization/configuration sequences as described above may be used in physiologic monitors comprising a microcontroller and connected discrete components. Such initialization sequences may be used in physiologic monitors that do not include digital control logic and other components as described above.

Figure 7:
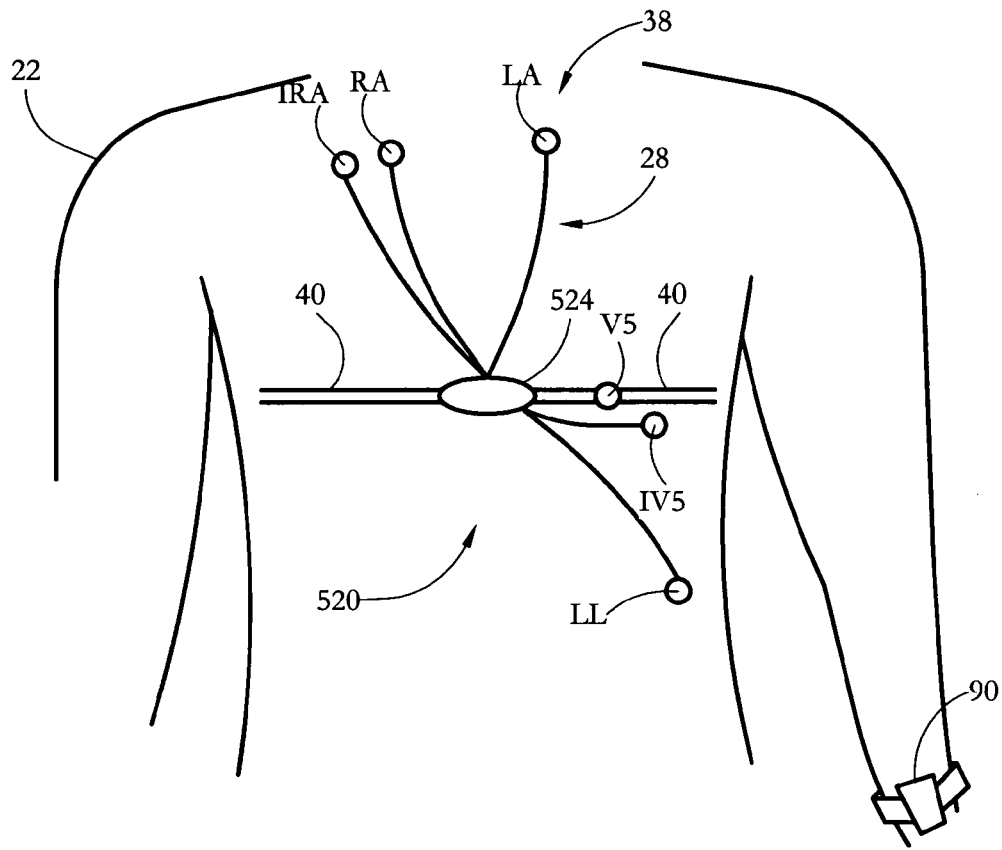
FIG. 7 shows a wearable physiologic monitor system including a wearable display connected to a wearable physiologic monitor, according to some embodiments of the present invention.

FIG. 7 shows a wearable physiologic monitor system 520 including a wearable display 90 connected to a wearable physiologic monitor 524 through a short-range wireless connection, according to some embodiments of the present invention. Display 90 may be worn by a subject on his/her wrist, and may include or form part of a watch capable of displaying a real time. The short-range wireless connections may be implemented using a standard such as a Class 2 (2.5 mW) Bluetooth specification, allowing connections over a distance of 10 meters. Alternatively, a wired connection may be used to minimize cost or unwanted RF radiation.

Figure 8:
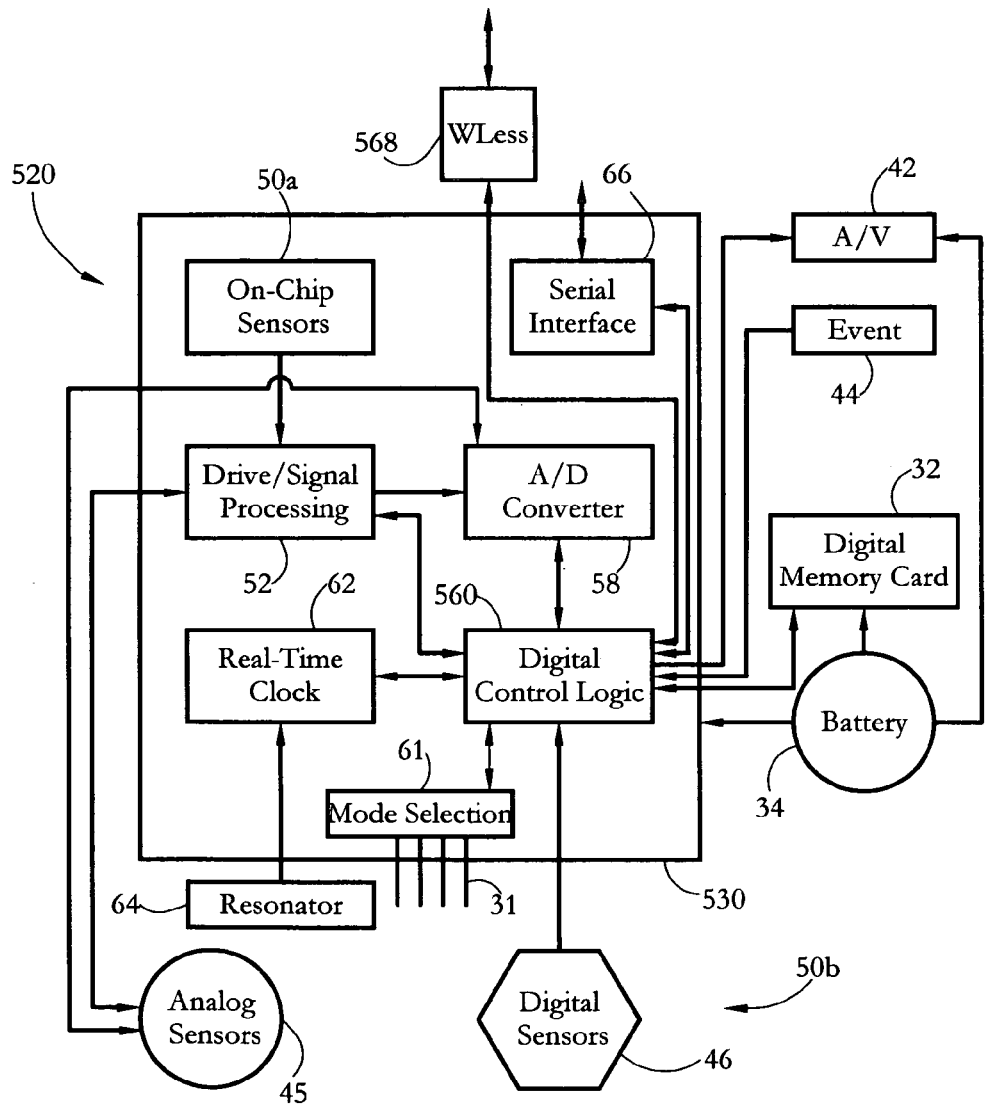
FIG. 8 is a diagram of the physiologic monitor of FIG. 7 according to some embodiments of the present invention.

FIG. 8 is a diagram of physiologic monitor 524 according to some embodiments of the present invention. Physiologic monitor 524 includes an integrated circuit 530 connected to an off-chip wireless interface 568. Wireless interface 568 may be connected to or include a wireless antenna, which is used to couple interface 568 to display 90. Wireless interface 568 is connected to digital control logic 560. Digital control logic 560 may include wireless packet assembly logic assembling physiologic data packets for transmission to display 90. The display data may include a subset of the sensor data types stored in digital memory 32, and may be sent to wireless interface 568 at more frequent or less frequent time intervals than the data packets stored in digital memory 32.

Figure 9:
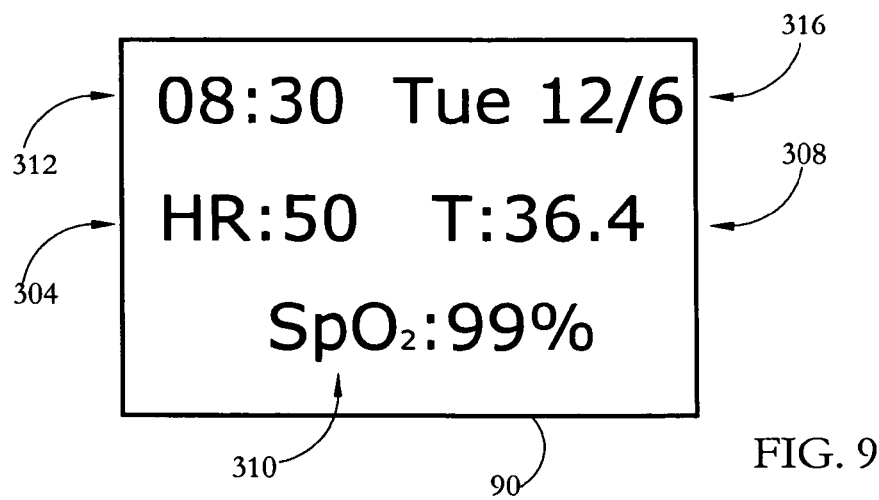
FIG. 9 shows an exemplary real-time display of physiologic data according to some embodiments of the present invention.

FIG. 9 shows an exemplary display 90 showing recorded real-time, time-dependent physiologic data according to some embodiments of the present invention. Display 90 presents to a user indications of several physiologic parameters determined by physiologic monitor 524 (FIG. 7), including a heart rate display 304, a current subject body temperature display 308, and a current subject blood oxygen level 310, among others. Display 90 also presents a real-time indicator 312 and a current date indicator 316. In some embodiments, display 90 may receive and display a time-dependent signal waveform or trend, such as a current ECG waveform covering a few seconds, or a heart rate plot sampled once a minute over one hour.

According to one aspect, preferred systems and method described above allow producing a compact, low-cost, wearable multi-parameter physiologic monitor. Such a monitor may include a disposable patch encapsulating physiologic sensors, a processing integrated circuit, and sensor interconnections. Signal processing circuitry, a real-time clock, an A/D converter, an I/O port, a digital memory interface, and digital control logic are integrated on a single integrated circuit, which provides signal conditioning, time-stamping, multi-data-rate stream processing, and data packet assembly for storage in a removable digital memory such as a flash memory card. Using an application-specific integrated circuit (ASIC) including integrated special-purpose signal conditioning circuitry and digital control logic, rather than a programmable microcontroller and discrete front-end circuitry, allows producing a compact, power-efficient physiologic monitoring patch than can be readily made disposable. Storing the data in a removable digital memory also allows a simplified integrated circuit design, allowing device portability without requiring relatively-complex, power-consuming wireless transmission circuitry. The digital memory may be reused with multiple physiologic monitoring patches, while the wearable patch and its incorporated sensors and ASIC may be discarded at regular intervals, e.g. every 24 hours.

According to one aspect, the same physiologic monitor and incorporated integrated circuit design may be used in multiple-modes, each of which may be selected upon manufacture of the physiologic monitor. In a stand-alone mode, the physiologic monitor digital control logic performs time-stamping and packet assembly, and stores data to the digital memory. The stand-alone mode is particularly suited to applications in which portability, disposability, and low-cost are of primary concern. In a set of peripheral modes, the monitor digital control logic is used in conjunction with a microcontroller, which may be mounted on the subject or disposed nearby (e.g. in a bedside, larger unit). Using a programmable microcontroller allows greater flexibility in the data processing performed, but reduces the portability and increases the cost of the monitoring system. The peripheral modes are particularly suited to more stable environments, for example for in-hospital, bedside uses. In a passive peripheral mode, the physiologic monitor digital control logic is essentially bypassed, and the microcontroller performs operations such as control of an A/D converter, time-stamping, and packet assembly. In a self-clocked peripheral mode, the physiologic monitor digital control logic sends hardware interrupts to the microcontroller to periodically transfer time-stamped, assembled data packets to the microcontroller. Allowing a single integrated circuit design to be used in multiple modes allows sharing common design and fixed costs for both simpler standalone applications and more complex, bedside applications. For such bedside applications, the integrated circuit effectively acts as a signal processing front end for a programmable microprocessor such as a microcontroller.

According to another aspect, an initialization sequence, initialization logic and initialization console, as well as other aspects described above may be used in physiologic monitoring systems using discrete components for signal conditioning circuitry and digital control logic, rather than systems using an integrated circuit as described above. According to another aspect, such an initialization approach may be used to initialize a microcontroller rather than hardwired digital control logic, for example in a system configured in a peripheral mode, or in a system otherwise using a programmable microcontroller. In such a system, an initialization sequence may be implemented using initialization software running on the microcontroller. The authenticated firmware-download aspects described above are of particular significance in a system using a microcontroller. According to another aspect, such an initialization approach may be used in a system using a fixed digital memory. In some embodiments, such an initialization approach allows flexible customization and monetization of a common design for different uses in the field, for example in a doctor's office, and allows reducing device piracy.

According to another aspect, exemplary circuitry as described above may be used in a wearable physiologic monitoring system including a case or other structure loosely attached to a subject (e.g. worn inside clothing, or hanging from the subject), rather than a patch adhered to the subject.

According to anther aspect, the present invention provides computer-readable media encoding instructions, and computer systems programmed with instructions to perform the initialization and/or configuration steps described above, as well as other physiologic monitoring steps.

According to another aspect, the present invention provides a kit comprising a reusable, removable digital memory and a plurality of disposable, wearable physiologic monitors as described above. For example, one digital memory may be provided together with 7 or 10 disposable physiologic monitors, each to be used by a subject for one day. The physiologic monitors provided in the kit are blank or otherwise user-inoperable to record subject physiologic data. The digital memory is pre-loaded with subject-specific physiologic monitor authorization and configuration data. The pre-loading may be performed for example in a physician's office, using an initialization console as described above, and according to subject-specific monitoring requirements. Connecting a blank physiologic monitor to the removable digital memory causes an activation and configuration of the physiologic monitor as described above. The activation results in the monitor becoming user-operable to record physiologic monitoring data. Subsequently, recorded physiologic monitoring data is stored in the removable digital memory.

According to some embodiments, a physiologic monitoring system as described above is employed in a long-term, patient-administered method of providing titration of care for a chronic disease, for which a compact, low-cost design as described above is of particular benefit. In an exemplary method, a physician issues one or more physiologic monitoring devices as described above to a patient in a first treatment state. The first treatment state may be a state in which the patient undergoes no treatment, or a state in which the patient undergoes a course of treatment, e.g. takes a particular medication. The patient uses the monitor(s) to record and store physiologic monitoring parameters over a period of days, weeks, or months, during a period of normal activity of the subject outside a medical facility. Such physiological monitoring may include detection of normal subject activity and physiologic parameters, as well as detection of less-common episodes such as syncope (fainting) or arrhythmias. Detected physiologic parameters may include the parameters described above, as well as parameters derived from measured data. For example, patient calorie expenditures due to physical activity may be estimated from recorded accelerometer data, while patient heart failure progression can be estimated using fluid load impedance measurements. Generating the data need not require the patient's return to a medical facility. Quantitative data generated over a period of time is used in conjunction with other data, including pre-treatment baseline data, to evaluate the effect of treatment on the patient, and to alter the course of therapy (e.g. medication dosages). New data for the altered course of therapy are then recorded. Quantitative data generated by different courses of treatment are then compared.

Quantitative data evaluation may include monitoring a time-dependence of relevant parameters as a course of treatment proceeds, comparing such measured parameters to pre-treatment baseline data, and evaluating effects of treatment changes on measured parameters. In some embodiments, quantitative data evaluation may include one or more of: comparing data during after/therapy to a pre-treatment baseline; comparing two or more medications or other treatments to each other; comparing two or more medications or other treatments to a pre-treatment baseline; comparing different dosages of one or more medications or other treatments, alone or in combination, to each other and/or to a pre-treatment baseline; comparing different combinations of medications or other treatments; evaluating non-medication treatment parameters, such as settings of implantable devices (e.g. pacemakers); evaluating implantable device settings in combination with one or more medications; comparing data recorded before and after surgical procedures. The preferred physiologic designs described above are particularly suited for such methods, and in particular for long-term (over weeks or months) tracking of patients' health by performing quantitative evaluations as described above.

Commonly available physiologic monitors such as Holter monitors are normally too complex and costly to permit convenient, widespread distribution of such monitors to patients for self-use outside of medical facilities. Qualitative evaluations by a patient (e.g. statements such as "I feel fine") are not particularly useful for evaluating subtle effects of medications or other treatment on the patient. A subject may go about his or her normal daily routines while data is recorded, and return to a physician's office at intervals spaced apart over a period of days or weeks to allow a physician to download stored physiologic data, perform a quantitative evaluation of the course of treatment according to the downloaded data, and adjust the course of treatment according to the evaluation.

According to another aspect, the basic physiologic monitor integrated circuit design supports multiple sensor types. The same physiologic monitor design may be used with multiple, different sensor subsets, as needed in a particular application, by enabling a desired sensor subset during the physiologic monitor manufacture or during an initialization of the physiologic monitor through an I/O (e.g. serial) port.

For more sophisticated data analysis, the digital memory may be removed from the physiologic monitor and connected to a personal computer or other device including a general-purpose CPU and associated analysis software. For example, a computer screen may be used to visualize data-intensive sensor displays such as time-dependent ECG traces.

In some embodiments, wireless transmission circuitry may be added to the physiologic monitor and connected to the data processing integrated circuit in order to provide a short-range connection to a wearable display unit. Adding wireless transmission circuitry to the physiologic monitor can add significant complexity, power losses, and noise to the system. Thus, a presently preferred implementation does not include wireless transmission circuitry.

Noise is of particular concern in systems measuring subject ECG signals, which may be on the order of 1 mV full-scale, and include frequencies of interest on the order of Hz. In addition to generally-present noise sources such as power lines, microwave and wireless sources, and electrolytic effects at the subject's skin, an integrated circuit designed as described above may also be affected by noise from an on-chip real-time clock tick signal or its harmonics. The effects of such noise on physiologic signal processing circuitry is preferably minimized by physically separating the real-time clock from the physiologic signal processing circuitry on opposite areas of a common substrate, and/or softening edges of a real-time tick signal, among others.

An integrated temperature sensor is also potentially subject to noise or extraneous inputs due to power losses from the integrated circuit itself, rather than heat emissions from the subject's skin. To minimize such noise sources, it is preferable to minimize the power losses from the integrated circuit, as well as optimize the thermal coupling between the temperature sensor and the subject.

It will be clear to one skilled in the art that the above embodiments may be altered in many ways without departing from the scope of the invention. For example, a physiologic monitoring system as described above may include some asynchronous circuitry or logic. In some embodiments, various connections may be used to connect a physiologic monitor to an external computer or microcontroller, including wired (e.g. serial, USB, parallel) and wireless (optical, RF) connections. Accordingly, the scope of the invention should be determined by the following claims and their legal equivalents.

What is claimed is:

1. A physiologic monitoring system including a physiologic monitoring application-specific integrated circuit, the integrated circuit comprising:

amplification and filtering circuitry integrated on a semiconductor substrate, for amplifying and filtering a set of electrical signals received from a first set of physiologic sensors to generate a first set of filtered electrical signals, the amplification and filtering circuitry comprising analog filtering circuitry for filtering the set of electrical signals received from the first set of physiologic sensors, wherein the first set of physiologic sensors is a set of electrocardiogram sensors, and wherein the set of electrical signals received from the first set of physiologic sensors is a set of electrocardiogram electrical signals;

a real-time clock integrated on the semiconductor substrate, the real-time clock comprising a divider chain configured to frequency-divide a base timing signal to generate a real-time clock tick, wherein a frequency of signals generated by the real-time clock is within a frequency range of electrocardiogram electrical signals processed by the amplification and filtering circuitry; and digital control logic integrated on the semiconductor substrate and connected to the real-time clock and the amplification and filtering circuitry;

the digital control logic being configured to receive a first set of digital physiologic data derived from the first set of filtered electrical signals, receive a second set of digital physiologic data, wherein the second set of physiologic data includes physiologic data sampled with a different sampling rate than the first set of digital physiologic data, generate a time-stamped physiologic data packet from a real-time indicator, the first set of digital physiologic data and the second set of digital physiologic data, wherein the real-time indicator is generated according to the real-time clock tick; and transmit the physiologic data packet for storage in a digital memory.

2. The system of claim 1, wherein the integrated circuit further comprises mode-selection logic integrated on the semiconductor substrate and connected to the digital control logic, for setting an operating mode of the integrated circuit to a mode selected from a stand-alone mode and a peripheral mode.

3. The system of claim 2, wherein the integrated circuit further comprises a set of integrated circuit mode-selection input pins connected to the mode-selection logic, wherein the mode-selection logic is configured to set the operating mode of the integrated circuit according to a set of logic levels of the mode-selection input pins.

4. The system of claim 3, wherein the mode-selection input pins are bonded to a set of mode-selection logic levels.

5. The system of claim 1, wherein the integrated circuit is integrated in a wearable patch configured to be attached to a subject's skin.

6. The system of claim 5, wherein the first set of physiologic sensors is integrated in the wearable patch.

7. The system of claim 5, wherein the patch comprises an encapsulant enclosing the integrated circuit.

8. The system of claim 5, further comprising an adhesive for coupling the patch to a subject's skin.

9. The system of claim 1, further comprising a physiologic temperature sensor thermally coupled to the subject and connected to the digital control logic, for generating a set of subject temperature indicators, wherein the second set of digital data comprises subject temperature data derived from the subject temperature indicators.

10. The system of claim 1, further comprising an accelerometer connected to the digital control logic, for generating a set of acceleration indicators, wherein the second set of digital data comprises acceleration data derived from the acceleration indicators.

11. The system of claim 10, wherein the integrated circuit comprises the accelerometer, the accelerometer being integrated on the semiconductor substrate.

12. The system of claim 1, wherein the integrated circuit further comprises an impedance measurement circuit coupled to the subject and connected to the digital control logic, for generating a set of impedance indicators, wherein the second set of digital data comprises subject impedance data derived from the impedance indicators, the impedance measurement circuit being integrated on the semiconductor substrate.

13. The system of claim 1, further comprising a pulse oximeter for generating a set of blood oxygen indicators, wherein the second set of digital data comprises blood oxygen data derived from the blood oxygen indicators.

14. The system of claim 1, further comprising a light detector for generating a set of ambient light intensity indicators, wherein the second set of digital data comprises ambient light intensity data derived from the ambient light intensity indicators.

15. The system of claim 1, further comprising a sound detector for generating a set of ambient sound intensity indicators, wherein the second set of digital data comprises ambient sound intensity data derived from the ambient sound intensity indicators.

16. The system of claim 1, further comprising an ionizing radiation detector for generating a set of ambient ionizing radiation indicators, wherein the second set of digital data comprises ambient ionizing radiation data derived from the ambient ionizing radiation indicators.

17. The system of claim 1, wherein the amplification and filtering circuitry comprises a pacemaker pulse detection circuit for detecting a set of pacemaker pulses sensed by the electrocardiogram electrodes.

18. The system of claim 1, wherein the amplification and filtering circuitry comprises continuous-time analog filtering circuitry.

19. The system of claim 1, wherein the amplification and filtering circuitry comprises switched capacitor filtering circuitry.

20. The system of claim 1, wherein the amplification and filtering circuitry comprises a digital signal processor.

21. The system of claim 1, further comprising a timing resonator coupled to the real-time clock, for generating the base timing signal.

22. The system of claim 21, wherein the timing resonator is integrated on the semiconductor substrate.

23. The system of claim 1, further comprising a subject sensory indicator device connected to the digital control logic, for providing a sensory indication to a subject.

24. The system of claim 23, wherein the sensory indicator device comprises a light-emitting device.

25. The system of claim 23, wherein the sensory indicator device comprises a speaker.

26. The system of claim 25, wherein the sensory indication comprises a voice prompt.

27. The system of claim 1, wherein the digital control logic comprises physiologic condition detection logic configured to activate a sensory indicator device when a physiologic parameter value meets a predetermined condition.

28. The system of claim 1, wherein the digital control logic comprises real-time detection logic configured to activate a sensory indicator device when a real time indicator meets a predetermined condition.

29. The system of claim 1, wherein the digital control logic comprises electrode fault detection logic for detecting an electrocardiogram electrode fault.

30. The system of claim 1, wherein the digital control logic is configured to include an external user-actuation signal in the time-stamped data packet.

31. The system of claim 1, further comprising a wearable visual display connected to the digital control logic, for generating a display of data derived from the physiologic data packet.

32. The system of claim 1, wherein the digital control logic is configured to generate a set of time-stamped data packets including a first time-stamped physiologic data packet, a second time-stamped physiologic data packet, and a set of non-time-stamped physiologic data packets, wherein the first time-stamped data packet and the second time-stamped data packet are temporally separated by the set of non-time-stamped physiologic data packets.

33. The system of claim 1, wherein the digital control logic is configured to assemble a set of physiologic data packets according to a predetermined inter-packet time period, wherein each packet in the set of physiologic data packets is separated by the inter-packet time period from an immediately preceding data packet and an immediately subsequent data packet.

34. The system of claim 1, wherein a signal shape of the real-time clock tick has softened edges.

35. The system of claim 1, wherein a frequency of the real-time clock tick is on the order of Hz.

36. The system of claim 1, wherein the real-time clock and the amplification and filtering circuitry are situated along opposite sides of the semiconductor substrate, so as to separate the real-time clock from the amplification and filtering circuitry along a surface of the semiconductor substrate.

37. The system of claim 1, further comprising a decoupling off-chip capacitor connected to the integrated circuit, for isolating the real-time clock from the amplification and filtering circuitry.

38. A wearable physiologic monitoring system comprising:
- a battery;
- a plurality of electrocardiogram electrodes to be applied to a subject;
- a removable digital memory; and
- an application-specific integrated circuit connected to the removable digital memory, the battery, and the plurality of electrocardiogram electrodes, the integrated circuit comprising:
  - amplification and filtering circuitry integrated on a semiconductor substrate and connected to the plurality of electrocardiogram electrodes, for amplifying and filtering a set of electrical signals received from the electrocardiogram electrodes to generate a set of filtered electrocardiogram data, the amplification and filtering circuitry comprising analog filtering circuitry for filtering the set of electrical signals received from the electrocardiogram electrodes;
  - a real-time clock integrated on the semiconductor substrate, the real-time clock comprising a divider chain configured to frequency-divide a base timing signal to generate a real-time clock tick, wherein a frequency of signals generated by the real-time clock is within a frequency range of electrocardiogram electrical signals processed by the amplification and filtering circuitry; and
  - digital control logic integrated on the semiconductor substrate and connected to the real-time clock and the amplification and filtering circuitry, the digital control logic being configured to
    - assemble a time-stamped data packet including a set of digital electrocardiogram data derived from the filtered electrocardiogram data, the data packet being time-stamped according to a real-time indicator generated according to the real-time clock tick, and
    - transmit the data packet for storage in the removable digital memory.

39. The system of claim 38, wherein the digital control logic is further configured to assemble the data packet to include a set of digital non-electrocardiogram physiologic data.

40. The system of claim 38, wherein the integrated circuit, battery, and removable digital memory are integrated in a wearable patch configured to be attached to a subject's skin.

41. The system of claim 40, wherein the plurality of electrodes are integrated in the wearable patch.

42. The system of claim 40, wherein the patch comprises an encapsulant enclosing the integrated circuit.

43. The system of claim 40, further comprising an adhesive for coupling the patch to a subject's skin.

44. The system of claim 38, wherein the amplification and filtering circuitry comprises a pacemaker pulse detection circuit for detecting a set of pacemaker pulses sensed by the electrocardiogram electrodes.

45. The system of claim 38, wherein the amplification and filtering circuitry comprises continuous-time analog filtering circuitry.

46. The system of claim 38, wherein the amplification and filtering circuitry comprises switched capacitor filtering circuitry.

47. The system of claim 38, wherein the amplification and filtering circuitry comprises a digital signal processor.

48. The system of claim 38, further comprising a timing resonator coupled to the real-time clock, for generating the base timing signal.

49. The system of claim 48, wherein the timing resonator is integrated on the semiconductor substrate.

50. The system of claim 38, further comprising a physiologic temperature sensor for generating a set of subject temperature indicators, the digital control logic being connected to the temperature sensor and configured to include in the time-stamped data packet a set of digital temperature data derived from the set of subject temperature indicators.

51. The system of claim 38, further comprising an accelerometer for generating a set of subject acceleration indicators, wherein the digital control logic is configured to include in the time-stamped data packet a set of digital acceleration data derived from the acceleration indicators.

52. The system of claim 51, wherein the integrated circuit comprises the accelerometer, the accelerator being integrated on the semiconductor substrate.

53. The system of claim 38, further comprising an impedance measurement circuit comprising an impedance measurement electrode, for generating a set of impedance indicators, wherein the digital control logic is configured to include in the time-stamped data packet a set of digital impedance data derived from the impedance indicators.

54. The system of claim 38, further comprising a pulse oximeter for generating a set of blood oxygen indicators, wherein the digital control logic is configured to include in the time-stamped data packet a set of digital blood oxygen data derived from the blood oxygen indicators.

55. The system of claim 38, further comprising a light detector for generating a set of ambient light intensity indicators, wherein the digital control logic is configured to include in the time-stamped data packet a set of digital ambient light data derived from the ambient light intensity indicators.

56. The system of claim 38, further comprising a sound detector for generating a set of ambient sound intensity indicators, wherein the digital control logic is configured to include in the time-stamped data packet a set of digital ambient sound data derived from the ambient sound intensity indicators.

57. The system of claim 38, further comprising an ionizing radiation detector for generating a set of ambient ionizing radiation indicators, wherein the digital control logic is configured to include in the time-stamped data packet a set of digital ionizing radiation data derived from the ambient ionizing radiation indicators.

58. The system of claim 38, further comprising a subject sensory indicator device connected to the digital control logic, for providing a sensory indication to a subject.

59. The system of claim 58, wherein the sensory indication comprises a voice prompt.

60. The system of claim 58, wherein the digital control logic comprises physiologic condition detection logic connected to the sensory indicator device and configured to activate the sensory indicator device when a physiologic parameter value meets a predetermined condition.

61. The system of claim 58, wherein the digital control logic comprises real-time detection logic connected to the sensory indicator device and configured to activate a sensory indicator device when a real time indicator meets a predetermined condition.

62. The system of claim 38, wherein the digital control logic comprises electrode fault detection logic connected to the plurality of electrocardiogram electrodes, for detecting an electrocardiogram electrode fault.

63. The system of claim 38, further comprising an external event actuator configured to generate an event signal in response to actuation by a subject, the digital control logic being configured to include digital event data derived from the event signal in the time-stamped data packet.

64. The system of claim 38, further comprising a wearable visual display connected to the digital control logic, for generating a display of data derived from the digital electrocardiogram data.

65. A wearable physiologic monitoring system comprising:
a battery;
a plurality of electrocardiogram electrodes to be applied to a subject;
a digital memory; and
an application-specific integrated circuit connected to the digital memory, the battery, and the plurality of electrocardiogram electrodes, the integrated circuit comprising:
    amplification and filtering circuitry integrated on a semiconductor substrate and connected to the plurality of electrocardiogram electrodes, for amplifying and filtering a set of electrical signals received from the electrocardiogram electrodes to generate a set of filtered electrocardiogram data, the amplification and filtering circuitry comprising analog filtering circuitry for filtering the set of electrical signals received from the electrocardiogram electrodes;
    a real-time clock integrated on the semiconductor substrate, the real-time clock comprising a divider chain configured to frequency-divide a base timing signal to generate a real-time clock tick, wherein a frequency of signals generated by the real-time clock is within a frequency range of electrocardiogram electrical signals processed by the amplification and filtering circuitry; and
    digital control logic integrated on the semiconductor substrate and connected to the real-time clock and the amplification and filtering circuitry, the digital control logic being configured to
        time-stamp a set of digital electrocardiogram data derived from the filtered electrocardiogram data according to a real-time indicator generated according to the real-time clock tick, and
        transmit a set of time-stamped digital electrocardiogram data for storage in the digital memory.

66. A physiologic monitoring system comprising:
electrocardiogram sensing means for sensing a set of electrocardiogram signals generated along a subject's skin;
wearable means connected to the electrocardiogram sending means and comprising:
    digital memory means; and
    an application-specific integrated circuit comprising
        signal conditioning means integrated on a semiconductor substrate, for amplifying and filtering a set of electrical signals received from the electrocardiogram sensing means;
        real-time means integrated on the semiconductor substrate, the real-time means comprising a divider chain configured to frequency-divide a base timing signal to generate a real-time clock tick, wherein a frequency of signals generated by the real-time means is within a frequency range of electrocardiogram electrical signals processed by the signal conditioning means; and
        digital control logic integrated on the semiconductor substrate and connected to the signal conditioning means, for time-stamping according to a set of real-time indicators a set of digital electrocardiogram data derived from the electrical signals, and transmitting a set of time-stamped digital electrocardiogram data to the digital memory means for storage, wherein the real-time indicators are generated according to the real-time clock tick.

67. A wearable physiologic monitoring system comprising:
a digital memory;
a wearable patch comprising an integrated circuit connected to a plurality of electrocardiogram electrodes and the digital memory, the integrated circuit comprising:
    a temperature sensor integrated on a semiconductor substrate, for generating a set of subject temperature indicators;
    an accelerometer integrated on the semiconductor substrate, for generating a set of subject acceleration indicators;
    amplification and filtering circuitry integrated on the semiconductor substrate and connected to the plurality of electrocardiogram electrodes, for amplifying and filtering a set of electrical signals received from the electrocardiogram electrodes, the amplification and filtering circuitry comprising analog filtering circuitry for filtering the set of electrical signals received from the electrocardiogram electrodes;
    a real-time clock integrated on the semiconductor substrate, the real-time clock comprising a divider chain configured to frequency-divide a base timing signal to generate a real-time clock tick, wherein a frequency of signals generated by the real-time clock is within a frequency range of electrocardiogram electrical signals processed by the amplification and filtering circuitry; and
    digital control logic connected to the amplification and filtering circuitry, the temperature sensor and the accelerometer, the digital control logic being configured to
        assemble a physiologic data packet including digital electrocardiogram data derived from the set of electrical signals, temperature data derived from the set of subject temperature indicators, and acceleration data derived from the subject acceleration indicators,
        time-stamp the data packet according to a real-time indicator generated according to the real-time clock tick, and
        transmit the data packet to the digital memory for storage.

68. A physiologic monitoring method comprising:
sensing a first set of physiologic indicators generated by a subject using a first sensor set, wherein the first sensor set is a set of electrocardiogram sensors, and wherein sensing the first set of physiologic indicators comprises sensing a set of electrocardiogram electrical signals; and employing a mixed analog and digital application-specific integrated circuit comprising signal conditioning circuitry, a real-time clock and digital control logic integrated on a semiconductor substrate to amplify and filter the first set of physiologic indicators, employ a divider chain of the real-time clock to frequency-divide a base timing signal to generate a real-time clock tick, wherein a frequency of signals generated by the real-time clock is within a frequency range of electrocardiogram electrical signals processed by circuitry of the integrated circuit used to amplify and filter and first set of physiologic indicators, generate a first set of digital physiologic data from the first set of physiologic indicators at a first sampling rate, assemble the first set of digital physiologic data into a data packet, time-stamp the data packet according to a real-time indicator generated according to the real-time clock tick, and transmit the data packet for storage in a removable digital memory connected to the integrated circuit.

69. The method of claim 68, further comprising:

sensing a second set of physiologic indicators generated by the subject using a second sensor set; and employing the integrated circuit to generate a second set of digital physiologic data from the second set of physiologic indicators at a second sampling rate different from the first sampling rate.

70. The method of claim 68, further comprising:

performing a first quantitative evaluation of an effect on the subject of a first course of therapy according to the first set of digital physiologic data;

selecting a second course of therapy for the subject according to the first quantitative evaluation; and performing a second quantitative evaluation of an effect of the second course of therapy on the subject.

71. The method of claim 70, wherein the first course of therapy comprises administering a first medication dose to the subject, and the second course of therapy comprises administering a second medication dose to the subject.

72. The method of claim 68, wherein a signal shape of the real-time clock tick has softened edges.

73. The method of claim 68, wherein a frequency of the real-time clock tick is on the order of Hz.

74. The method of claim 68, wherein the real-time clock and the amplification and filtering circuitry are situated along opposite sides of the semiconductor substrate, so as to separate the real-time clock from the amplification and filtering circuitry along a surface of the semiconductor substrate.

75. The method of claim 68, further comprising isolating the real-time clock from the amplification and filtering circuitry using a decoupling off-chip capacitor connected to the integrated circuit.

* * * * *